United States Patent [19]

Noda et al.

[11] Patent Number: 5,320,853

[45] Date of Patent: Jun. 14, 1994

[54] CONTROLLED RELEASE FORMULATION FOR PHARMACEUTICAL COMPOUNDS

[75] Inventors: Kazuo Noda; Yoshiyuki Hirakawa, both of Hyogo; Hiroyuki Yoshino, Osaka, all of Japan; David D. MacLaren, Overland Park, Kans.; Paul F. Skultety, Leawood, Kans.; John R. Lefler, Overland Park, Kans.; Greg M. Beck, Lee's Summit, Mo.

[73] Assignee: Merrell Dow Pharmaceuticals Inc., Cincinnati, Ohio

[21] Appl. No.: 995,309

[22] Filed: Dec. 22, 1992

Related U.S. Application Data

[63] Continuation of Ser. No. 702,854, May 20, 1991, abandoned.

[51] Int. Cl.$^5$ .......................... A61K 9/24; A61K 9/58
[52] U.S. Cl. ................................ 424/472; 424/462; 424/471; 424/482; 424/497
[58] Field of Search ............... 424/462, 472, 482, 497, 424/471

[56] References Cited

U.S. PATENT DOCUMENTS

| | | | |
|---|---|---|---|
| 2,928,770 | 3/1960 | Bardani | 167/82 |
| 3,562,257 | 2/1971 | Kugita et al. | 260/239.3 |
| 3,917,813 | 11/1975 | Pedersen | 424/20 |
| 3,954,959 | 5/1976 | Pedersen | 424/21 |
| 4,361,546 | 11/1982 | Stricker et al. | 424/19 |
| 4,367,217 | 1/1983 | Gruber et al. | 424/19 |
| 4,427,648 | 1/1984 | Brickl et al. | 424/16 |
| 4,438,091 | 3/1984 | Gruber et al. | 424/21 |
| 4,459,279 | 7/1984 | Stricker et al. | 424/19 |
| 4,567,175 | 1/1986 | Takeda et al. | 514/211 |
| 4,596,705 | 6/1986 | Schepky et al. | 424/35 |
| 4,610,870 | 9/1986 | Jain et al. | 424/19 |
| 4,663,150 | 5/1987 | Panoz et al. | 424/494 |
| 4,716,040 | 12/1987 | Panoz et al. | 424/459 |
| 4,721,619 | 1/1988 | Panoz et al. | 424/459 |
| 4,724,148 | 2/1988 | Sonobe et al. | 424/480 |
| 4,726,951 | 2/1988 | Panoz et al. | 424/465 |
| 4,765,988 | 8/1988 | Sonobe et al. | 424/468 |
| 4,820,521 | 4/1989 | Panoz et al. | 424/458 |
| 4,826,688 | 5/1989 | Panoz et al. | 424/458 |
| 4,894,240 | 1/1990 | Geoghegan et al. | 424/497 |
| 4,963,365 | 10/1990 | Samejima et al. | 424/466 |
| 5,055,306 | 10/1991 | Barry et al. | 424/482 |

FOREIGN PATENT DOCUMENTS

| | | | |
|---|---|---|---|
| 0225085 | 6/1987 | European Pat. Off. | A61K 31/49 |
| 2802114 | 7/1979 | Fed. Rep. of Germany | A61K 9/24 |
| 0615010 | 1/1986 | Japan | A61K 9/00 |
| 0768512 | 2/1957 | United Kingdom | |
| 0874586 | 8/1961 | United Kingdom | |
| 1346610 | 2/1974 | United Kingdom | A61J 3/10 |

OTHER PUBLICATIONS

K. Thoma, et al., Delaying The Release of Weak Basic Drugs, *Pharm. Ind.*, 51(1), 98–101 (1989).

*Primary Examiner*—Thurman K. Page
*Assistant Examiner*—Jyothsna Venkat
*Attorney, Agent, or Firm*—Michael J. Sayles

[57] ABSTRACT

Controlled release pharmaceutical beads are provided having a multi-layered core and a multi-layered periphery. The core contains at least (A) an inner portion having a suitable organic acid and (B) a sustainably-acid-releasing coating thereover. The periphery contains at least (A) an inner portion having a mixture of at least (i) a pharmaceutical compound and (ii) a surface-active agent, and (B) a sustainably-drug-releasing exterior coating.

11 Claims, 10 Drawing Sheets

CONTROLLED RELEASE FORMULATION FOR PHARMACEUTICAL COMPOUNDS

This is a continuation of application Ser. No. 07/702,854, filed May 20, 1991, now abandoned.

BACKGROUND OF THE INVENTION

This invention concerns multi-layered, controlled releasing drug beads, their preparation, and pharmaceutical use.

It is desirable to formulate orally delivered drugs in a manner which permits administration on a once or twice per day schedule to facilitate patient compliance and to reduce swings in blood plasma levels. However, it is difficult to achieve the desired therapeutic blood levels of many drugs, such as those which are rapidly absorbed into the bloodstream or those which are readily metabolized, without a more frequent dosing schedule. Desired blood levels of some of these drugs, however, can be obtained by formulating the drugs in a manner which delays or sustains the release of the drug.

Sustained release pharmaceutical preparations utilized to delay the release of a drug in the digestive tract include those in which the active substance is embedded within a polymeric matrix which dissolves extremely slowly. The drug is bound within the polymeric matrix and is gradually released as the matrix dissolves. In another type of delayed-release formulation, the active substance is shaped into beads or tablets and a sustained release coating is applied to slow the release of the active substance. The sustained release coating may be one which is soluble or it may be insoluble but permeable to an aqueous medium.

These conventional types of sustained release formulations can be effective to provide the desired release rates for some types of drugs, including those which are readily absorbed and/or metabolized. The human digestive tract, however, has pH values ranging from 1.0 to 7.5 and adequate blood levels of many types of drugs are difficult to achieve, even with such sustained release formulations. For example, drugs which are weak bases are solubilized and absorbed only if the solid pharmaceutical preparation remains in the acidic range for a sufficient time period. Absorption of such drugs thus depends greatly upon the retention time and the pH in the patient's stomach and upper intestine.

In order to obtain a pH independent release for drugs having pH dependent solubility characteristics, it has been suggested that the sustained release drug pellets or tablets include an acid buffer to provide the desired pH within the pellets regardless of the pH of the surrounding aqueous medium. It has proven difficult, however, to maintain the acid buffer for the time period necessary to achieve complete release of the drug from the pellets or tablet.

What is lacking and needed in the art is a controlled and pH independent release formulation which can be used for oral delivery of pharmaceuticals, particularly those pharmaceuticals which are generally soluble only in acidic mediums, and which is suitable for administration at infrequent intervals such as once or twice a day.

SUMMARY OF THE INVENTION

This invention provides, in one aspect, a pharmaceutical bead providing controlled and high percentage release of a drug, said pharmaceutical bead comprising components of 1) a multi-layered core, and
2) a multi-layered periphery, said core containing at least (A) an inner portion having a suitable hydrocarbyl or substituted hydrocarbyl carboxylic acid and (B) a sustainably-acid-releasing coating thereover, said periphery containing at least (A) an inner portion having a mixture of at least (i) a pharmaceutical compound and (ii) a surface-active agent, and (B) a sustainably-drug-releasing coating thereover, said bead having amounts of said components such as are effective for a generally pH independent controlled release of a high percentage of the pharmaceutical compound in a suitable aqueous media.

The bead may be formulated to provide a controlled release which is gradual and sustained. Alternately, the bead may be formulated to provide a controlled release which is rapid after a predetermined lag time. The beads may be advantageously formulated to provide a once or twice-a-day dosage. Beads having different release rates and/or lag times may be blended together to achieve the desired release rate and profile.

Another aspect of the invention is a process for preparing a controlled release pharmaceutical bead comprising building up an inner core portion containing a suitable hydrocarbyl or substituted hydrocarbyl carboxylic acid, coating it with a sustainably-acid-releasing coating to provide a multi-layered core, building upon said core an inner periphery of a mixture of at least a pharmaceutical compound and a surface-active agent, and coating it with a sustainably-drug-releasing coating.

A further aspect is a method for administering a pharmaceutical compound to a patient comprising orally ingesting a sample of controlled release pharmaceutical bead(s) such that a generally pH independent controlled release of the pharmaceutical compound is effected.

This invention is pharmaceutically useful.

Distinguishing features of the present invention include, with particular respect to the bead composition aspect, its core, containing the suitable acid component, e.g., of succinic acid, the acid optionally layered onto a substantially inert seed, e.g., a nonpareil sugar seed, and coated with the sustainably-acid-releasing layer, e.g., of ethylcellulose and hydroxypropylmethyl cellulose (HPMC), and so forth and the like, upon which is its periphery, containing the mixture of the pharmaceutical compound, e.g. clentiazem, and surface-active agent, e.g., sodium lauryl sulfate the mixture optionally containing suitable hydrocarbyl or substituted hydrocarbyl carboxylic acid, e.g., succinic acid, and coated with the sustainably-drug-releasing layer, e.g., of polymeric lacquer substances based on acrylates and/or methacrylates such as those polymers sold under the Eudragit trademark by Rohm Pharma GmbH, and so forth and the like.

Notably, the core can sustainably release its acid component into the periphery to provide a long lasting microenvironment suitable for solubilizing the pharmaceutical compound, especially those compounds which are weak bases. Moreover, the efficient release of the pharmaceutical compound, generally independent of pH, typically even at higher pH values, allows for dosing of the drug on a once-a-day schedule. Further, a highly desirable stair-stepped release profile may be obtained from a mixture of fast release beads of the present invention which have differing, preselected release time lags.

Further advantages attend this invention.

BRIEF DESCRIPTION OF THE DRAWINGS

In the drawings which form part of the specification hereof.

DESCRIPTION OF THE PREFERRED EMBODIMENTS

Figure 1:
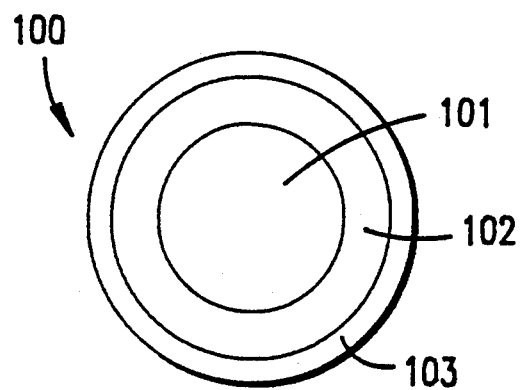
FIG. 1 is a cross-sectional schematic view of an inner core of a bead of this invention.

The controlled release pharmaceutical bead of this invention comprises a multi-layered core and a multi-layered periphery. The core, or core component, contains at least (A) an inner portion having a hydrocarbyl or substituted hydrocarbyl carboxylic acid and (B) a sustainably-acid-releasing coating thereover.

As used herein, the term hydrocarbyl means consisting of hydrogen and carbon atoms, and when used in connection with carboxylic acid or esters or salts, includes oxygen atoms. The suitable hydrocarbyl or substituted hydrocarbyl carboxylic acids are generally solids, which, in conjunction with the surface-active agent, increase the co-solubility of the pharmaceutical compound. These acids are organic compounds, otherwise hydrocarbons, substituted only with carboxy group(s). The substituted hydrocarbyl carboxylic acids are hydrocarbyl carboxylic acids having further organic, notably, fully saturated organic, substitution(s) thereon. Preferably, the suitable hydrocarbyl or substituted hydrocarbyl carboxylic acid is an alkyl or substituted alkyl carboxylic acid. The alkyl carboxylic acid is a hydrocarbyl carboxylic acid, which is fully saturated save for the carboxy group(s) thereon. The substituted alkyl carboxylic acid is a substituted hydrocarbyl carboxylic acid, which is fully saturated except for the acid group(s) thereon. Advantageously, a plurality of carboxy functionalities is present in the acid.

Examples of suitable hydrocarbyl carboxylic acids, as alkyl carboxylic acids, include succinic, maleic, adipic, malic, tartaric, and citric acids. Succinic acid is the preferred hydrocarbyl carboxylic acid.

The sustainably-acid-releasing coating is a coating which allows sustained release of the acid component therethrough from the inner portion of the core of the bead. This coating allows release of the acid component of the inner portion of the core into the inner portion component of the peripheral portion of a complete bead of this invention. Preferably, this coating allows the acid component of the inner portion of the bead to release into the inner portion of the periphery of the bead at a substantially linear rate, which rate is slower than the release of the pharmaceutical compound through the sustainably-drug-releasing coating. This ensures the presence of acid in the inner portion of the bead periphery until all or substantially all of the compound has been released into the surrounding aqueous medium.

The sustainably-acid-releasing coating may be polymeric and may include water insoluble polymers which are generally impermeable to water in combination with a minor proportion of water soluble and/or water permeable polymers. The sustainably-acid-releasing coating may alternately include water insoluble polymers which are slightly permeable to water, alone or in combination with a minor proportion of water soluble and/or water permeable polymers.

The water insoluble polymers may include water insoluble cellulosics such as ethylcellulose, cellulose acetate, cellulose propionate (lower, medium or higher molecular weight), cellulose acetate propionate, cellulose acetate butyrate, cellulose acetate phthalate and cellulose triacetate. Ethylcellulose is the preferred cellulosic, especially ethylcellulose having an ethoxy content of 44 to 55%. It is preferred to use ethylcellulose in the form of an alcoholic solution.

The ethylcellulose or other cellulosic may be used in combination with a water soluble polymer such as hydroxypropylmethylcellulose (HPMC), particularly HPMC having a molecular weight of from about 10,000 to 20,000 atomic mass units, and/or hydroxypropylcellulose (HPC). A suitable ratio of ethylcellulose to water soluble polymer is from 99:1 to 9:1 by weight. Suitable plasticizers such as acetyl triethyl citrate and/or acetyl tributyl citrate can also be admixed with the ethylcellulose.

A particularly preferred sustainably-acid-releasing coating comprises an alcoholic solution of ethylcellulose and HPMC in a ratio of 10:1.

Suitable water insoluble polymers which are slightly water permeable include acrylic resins comprising copolymers synthesized from acrylic and methacrylic acid esters (e.g., the copolymer of acrylic acid lower alkyl ester and methacrylic acid lower alkyl ester) containing about 0.02 to 0.03 mole of a tri (lower alkyl) ammonium group per mole of the acrylic and methacrylic monomers used. An example of a suitable acrylic resin is a polymer manufactured by Rohm Pharma GmbH and sold under the Eudragit ™ RS trademark. Eudragit ™ RS is a water insoluble, water slightly permeable copolymer of ethyl acrylate (EA), methyl methacrylate (MM) and trimethylammoniumethyl methacrylate chloride (TAM) in which the molar ratio of TAM to the remaining components (EA and MM) is 1:40. It is preferred that acrylic resins such as Eudragit ™ RS by used in the form of an aqueous suspension.

Water insoluble/slightly permeable polymers such as Eudragit ™ RS may be used together with a water insoluble polymer which is freely water permeable, such as the Eudragit ™ RL acrylic resin copolymer manufactured by Rofun Pharma GmbH. Eudragit ™ RL consists of the same components as Eudragit ™ RS, except that the molar ratio of TAM to the remaining components (EA and MM) is 1:20. A suitable ratio of Eudragit ™ RS to the freely water permeable polymer such as Eudragit ™ is from 99:1 to 85:15, especially about 95:5, by weight. Suitable plasticizers such as acetyl triethyl citrate and/or acetyl tributyl citrate can also be admixed with the water insoluble polymers such as Eudragit ™ RS.

The periphery, or peripheral component, contains at least (A) an inner portion having a mixture containing at least (i) a pharmaceutical compound and (ii) a surface-active agent, and (B) a sustainably-drug-releasing coating thereover.

The pharmaceutical compound may include vitamins, amino acids, peptides, chemotherapeutics, antibiotics, agents affecting respiratory organs, antitussive expectorants, antitumor agents, autonomic drugs, neuropsychotropic agents, muscle relaxants, drugs affecting digestive organs, antihistamic agents, antidotes, hypnotic sedatives, antiepileptics, antipyretic analgesic antiphlogistics, cardiotonics, antiarrhythmics, hypotensive diuretics, vasodilators, hypolipidemic agents, alimentary analeptics, anticoagulants, hepatics, blood sugar-lowering agents, hypotensive agents, and other drugs which can be formulated and sustainably released in accordance with the practice of this invention. The pharmaceutical compound may be a single such drug or mixtures thereof.

As an example, the pharmaceutical compound may comprise a pharmaceutically acceptable benzothiazeine compound, to include pharmaceutically acceptable salt(s) thereof, selected from a compound represented by the following general formula:

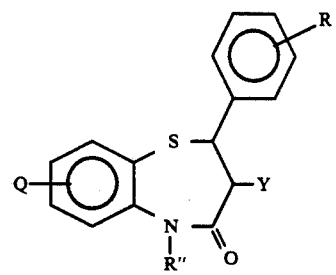

wherein
Q is hydro (H) or halo to include fluoro (F) and chloro (Cl), notably H or 8-Cl, and especially 8-Cl:

R is H, lower alkoxy, lower haloalkyl, cyano (CN), lower alkyl to include methyl (CH$_3$) or halo to include F and Cl, especialy H, methoxy (OMe), trifluoromethyl (CF$_3$) or CN;

Y is
OR', wherein R' is H or alkylacyl to include, e.g., lower alkylacyl and adamantylcarboxy, etc., notably H or lower alkylacyl to include groups such as acetyl, propionyl, butyryl, pivalyl, valeryl, isovaleryl, etc., especially acetyl, provided that then there is full saturation between carbons 2 and 3 of the benzothiazepine nucleus and 2,3-dihydro-functionality thereat as well, or Cl, provided that then there is ethylenic unsaturation between positions 2 and 3 of the benzothiazepine nucleus, and R" is 2-[di(lower alkyl)amino]ethyl (R"1), 3-[di(-lower alkyl)amino]propyl (R"2), 2-(pyrrolidino)ethyl (R"3), 3-(pyrrolidino)propyl (R"4), 2-(piperidino)ethyl (R"5), 3-(piperidino)propyl (R"6), 2-(morpholino)ethyl (R"7), 3-(morpholino)-propyl (R"8) or (N-pyridinium)alkyl with a suitable counterion being present (+R"9-X), notably R"1, especially with, e.g., R"2 being 2-(dimethylamino)ethyl (R"1a), or with R"1 being 2-(diisopropylamino)ethyl (R"1b), or R"3, or R"5, or +R"9-X, notably with +R"9-X being 2-(N-pyridinium)ethyl with a bromide and/or chloride counterion being present (+R"9a-X).

Suitable pharmaceutically acceptable salts generally include the hydrochloride, the fumarate, the maleate, the sulfate, the citrate, and so forth.

Of particular interest are diltiazem and clentiazem. Clentiazem is also known as 8-chlorodiltiazem and is chemically described as (+)cis(2S,3S)-3-(acetoxy)-8-chloro-5-[2-(dimethylamino)ethyl]-2,3-dihydro-2-(4-methoxyphenyl)-1,5-benzothiazepin-4(5H) one maleate.

The controlled release pharmaceutical bead of the present invention is particularly well adapted for use with those pharmaceutical compounds having a solubility significantly dependent on pH, especially those compounds which are weak bases and/or are poorly soluble or insoluble at the higher pH values encountered in the human digestive tract. By way of example, pharmaceutical compounds such as noscapine, paparefine, codeine, theophylline, clentiazem, and hydrochlorothiazide are weak bases and/or are moderately to practically insoluble in water and are particularly well-suited for formulation and delivery by the present invention. The surface-active agent is any compound or composition, which, when in admixture with the pharmaceutical compound in the bead of this invention, assists in the release of the pharmaceutical compound from the bead. As such, a wide variety of surfactants can be used. For example, such surfactants include nonionic surfactants such as sorbitan fatty acid ($C_{12}$–$C_{18}$) ester, glycerol fatty acid ($C_8$-$C_{18}$) ester, propylene glycol fatty acid ($C_8$-$C_{18}$) ester, sucrose fatty acid ($C_{12}$-$C_{18}$) ester, polyoxyethylene sorbitol fatty acid ($C_{12}$–$C_{18}$) ester, polyoxyethylene fatty acid ($C_{12}$-$C_{18}$) ester, trialkyl ($C_{12}$-$C_{18}$) phosphate, polyoxyethylene alkyl ($C_8$-$C_9$) phenyl ether and polyoxyethylenepolyoxpropylene block copolymer; anionic surfactants such as dialkyl ($C_5$-$C_8$) alkali metal sulfosuccinate and fatty acid ($C_8$-$C_{24}$) metal salt (i.e., metallic soap); and phospholipids. More specifically, the surfactants which can be used in the present invention include sorbitan fatty acid ($C_{12}$-$C_{18}$) ester such as sorbitan monolaurate, sorbitan sesquilaurate, sorbitan trilaurate, sorbitan monooleate, sorbitan sesquioleate, sorbitan monostearate; glycerol fatty acid ($C_8$-$C_{18}$) ester such as glycerol monocaprylate, glycerol monolaurate, glycerol dilaurate, glycerol monooleate; propylene glycol gatty acid ($C_8$-$C_{18}$) ester such as propylene glycol monocaprylate, propylene glycol monolaurate, propylene glycol monooleate; sucrose fatty acid ester having a HLB of 1 to 6 such as a mono-, di- or tri-ester of sucrose and myristic, palmitic or stearic acid or a mixture thereof; polyoxyethylene sorbitol fatty acid ($C_{12}$-$C_{18}$) ester having a HLB of not higher than 6 such as polyozyethylene sorbitol hexastearate; polyoxyethylene fatty acid ($C_{12}$-$C_{18}$) ester having a HLB of not higher than 6 such as polyoxyethylene monooleate; trialkyl ($C_{12}$-$C_{18}$) phosphate, such as trioleyl phosphate, trilauryl phsophate; polyoxyethylene alkyl ($C_8$-$C_9$) phenyl ether having a HLB of not higher than 6 such as polyoxyethylene nonylphenyl ether, polyoxyethylene octylphenyl ether; dialkyl ($C_5$-$C_8$) alkali metal sulfosucciniate such as di-n-hexyl sodiumsulfosuccinate, diamyl sodiumsulfosuccinate, bis(1-methylamyl) sodiumsulfosuccinate, bis(2-ethylhexyl) sodiumsulfosuccinate; metallic soap such as aluminium monostearate, aluminum distearate, aluminium tristearate, iron tristearate, calcium stearoyl-2-lactylate; and phospholipids such as soybean phospholipid, egg yolk phospholipid, phosphatidylethanolamine, phosphatidylcholine, phosphatidylserine, and inusitolphosphatide. Preferably, the surface-active agent comprises sodium lauryl sulfate.

The substantially-drug-releasing coating is a coating which allows sustained and controlled release of the pharmaceutical compound from the bead.

The sustainably-drug-releasing coating may be polymeric and may include water insoluble polymers which are slightly permeable to water and water insoluble polymers which are generally impermeable to water in combination with a minor proportion of water soluble and/or water permeable polymers.

Suitable water insoluble polymers which are slightly water permeable include acrylic resins comprising copolymers synthesized from acrylic and methacrylic acid esters (e.g., the copolymer of acrylic acid lower alkyl ester and methacrylic acid lower alkyl ester) containing about 0.02 to 0.03 mole of a tri (lower alkyl) ammonium group per mole of the acrylic and methacrylic monomers used. An example of a suitable acrylic resin is a polymer manufactured by Rohm Pharma GmbH and sold under the Eudragit TM RS trademark. Eudragit TM RS is a water insoluble, water slightly permeable copolymer of ethyl acrylate (EA), methyl methacrylate (MM) and trimethylammoniumethyl methacrylate chloride (TAM) in which the molar ratio of TAM to the remaining components (EA and MM) is 1:40. It is preferred that acrylic resin such as Eudragit TM RS by used in the form of an aqueous suspension.

Eudragit TM RS may be used together with a water-insoluble polymer which is freely water permeable, such as the Eudragit TM RL acrylic resin copolymer manufactured by Rohm Pharma GmbH. Eudragit TM RL consists of the same components as Eudragit TM RS, except that the molar ratio of TAM to the remaining components (EA and MM) is 1:20. A suitable ratio of Eudragit TM RS to the freely water permeable polymer such as Eudragit TM RL is from 99:1 to 85:15, especially about 95:5, by weight. Suitable plasticizers such as acetyl triethyl citrate and/or acetyl tributyl citrate can also be admixed with the Eudragit TM coating.

A particularly suitable sustainably-drug-releasing coating comprises an aqueous dispersion of Eudragit RS in combination with a minor proportion of Eudragit RL, preferably in a ratio of 95:5.

The water insoluble polymers may include water insoluble cellulosics such as ethylcellulose, cellulose acetate, cellulose propionate (lower, medium or higher molecular weight), cellulose acetate propionate, cellulose acetate butyrate, cellulose acetate phthalate and cellulose triacetate. The preferred cellulosic is ethylcellulose, especially ethylcellulose having an ethoxy content of 44 to 55%. It is preferred to use ethylcellulose in the form of an aqueous suspension, preferably in the form of an aqueous polymeric dispersion available from FMC Corporation under the Aquacoat ® trademark.

The ethylcellulose or other cellulosic may be used in combination with a water soluble polymer such as hydroxypropylmethylcellulose (HPMC), particularly HPMC having a molecular weight of from about 10,000 to 20,000 atomic mass units, and/or hydroxypropylcellulose (HC). A suitable ratio of ethylcellulose to water soluble polymer is from 99:1 to 90:10 by weight. Suitable plasticizers such as acetyl triethyl citrate and/or acetyl tributyl citrate can also be admixed with the ethylcellulose.

Use of the Eudragit TM RS sustainably-drug-releasing coating, alone or in combination with Eudragit TM RL polymer, is preferred to obtain a rapid release of the pharmaceutical compound after a preselected time delay or lag time. When placed in an aqueous medium, the Eudragit TM RS coated bead does not release the pharmaceutical compound contained therein until substantially complete hydration of the Eudragit TM coating is achieved. Once the coating has been completely hydrated, the pharmaceutical compound is rapidly released through the coating into the surrounding aqueous medium. The lag time in release of the pharmaceutical compound can be selected by varying the thickness of the sustainably-drug-releasing coating and/or by varying the amount of Eudragit TM RL polymer in the coating.

Optional components may be present in either or both the multi-layered core and periphery.

For example, in addition to the required component(s) of the inner portion of the core portion of the bead, there may be present a seed, e.g., a non-pareil sugar and/or starch seed, onto which the acid is layered. Such a seed is advantageously present.

As another example, in addition to the required components of the mixture of the inner portion of the peripheral portion of the bead, there may be present, selected independently at each or any occurrence, suitable hydrocarbyl or substituted hydrocarbyl carboxylic acid(s), to include alkyl or substituted alkyl carboxylic acid(s). Such another acid, e.g., the same acid as is employed in the inner core, is advantageously present.

In addition, various fillers such as talc and/or silicon dioxide, and/or a binder which includes ethylcellulose, stearic acid, white wax, and castor oil, may be present, such as in the inner core acid portion of the bead. A filler such as talc and/or silicon dioxide, e.g., colloidal silicon dioxide, and/or a binder which includes HPMC and talc may be present, such as in the inner portion of the periphery of the bead. Various excipients such as talc and/or magnesium stearate may also be present, such as in the sustainably-drug releasing coating and/or the sustainably-acid-releasing coating.

In reference to the drawings, and specifically FIG. 1, an inner core 100 comprises a seed 101, suitable hydrocarbyl or substituted hydrocarbyl carboxylic acid 102, and a sustainably-acid-releasing coating 103.

Figure 2:
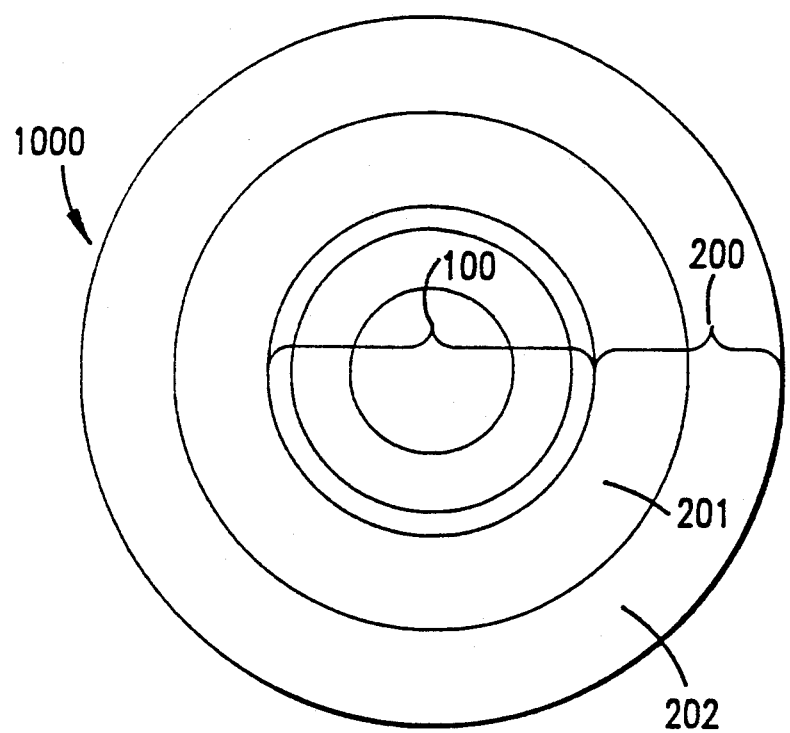
FIG. 2 is a cross-sectional schematic view of a complete bead of this invention; 100 represents the inner core; 101 represents the inner portion of the inner core; 102 and 103 represent the sustainably acid-releasing coating; 200 represents the periphery; 201 represents the inner portion of the periphery; 202 represents the sustainably drug-releasing coating; and 1000 represents the bead.

Turning to FIG. 2, a complete or finished bead 1000 comprises the inner core 100 and a periphery 200 which includes an inner peripheral portion mixture 201 and a sustainably-drug-releasing coating 202.

In general, the bead of this invention has amounts of its components such as are effective for the generally pH independent sustained and controlled release of the pharmaceutical compound in a suitable aqueous media. However, the following table describes more particular amounts of components in preferred bead formulations hereof. All parts or percentages are on a weight basis as a percentage of the whole bead formulation.

TABLE I

| Component | Wider Range | Narrower Range |
| --- | --- | --- |
| Core | 15 to 65% | 25 to 40% |
| Seed | 0 to 15% | 8.0 to 12.0% |
| Inner Portion | 10 to 45% | 10 to 25% |
| Inner Core Acid | 10 to 40% | 11 to 21% |
| Filler, e.g.: | | |
| Talc | 0.4 to 5% | 0.4 to 1.2% |
| Silicon Dioxide | 0.04 to 0.4% | 0.06 to 0.12% |
| Binder (w. wax, castor oil, stearic acid) | 0.3 to 1.7% | 0.4 to 1.1% |
| SAR Coating | 1 to 6% | 2 to 4% |
| Periphery | 35 to 90% | 60 to 75% |
| Inner Portion | 15 to 70% | 36 to 60% |
| Pharmaceutical Cpd. | 10 to 45% | 24 to 40% |
| Surface-Active Agent | 0.2 to 1.4% | 0.8 to 1.2% |
| Acid | 0 to 30% | 10 to 16% |
| Filler, e.g.: | | |
| Talc | 1 to 5% | 2 to 3% |
| Silicon Dioxide | 0.1 to 0.5% | 0.2 to 0.3% |
| Binder (HPMC, talc) | 0.4 to 1.8% | 0.9 to 1.3% |
| SDR Costing | 10 to 35% | 11 to 30% |

Samples of beads of this invention can have any weight and size distribution of individual beads allowing for the desired drug-releasing effect within the practice of this invention.

The suitable aqueous media can be water, a solution composed of water and hydrochloric acid, a solution composed of water and hydrochloric acid, say, further containing potassium chloride, at a pH of 1.2, a solution composed of water and sodium hydroxide, say, further buffered with potassium dihydrogen phosphate to a pH of 7.5, gastric juices, e.g., of the stomach and/or of the intestines. In testing, the water, HCl and KCl, pH 1.2, and the water, NaOH, $KH_2PO_4$, pH 7.5, solutions are preferred.

Preferred drug-release characteristics as a percent of pharmaceutical compound released in accordance with the practice of this invention generally include that more than about 80 percent of the pharmaceutical compound be thus released. Release of at least about 90 percent of the pharmaceutical compound is more preferred.

Preparation of the beads can be by known methods such as bead building in a CF granulator, for example a Freund TM CF granulator, or a conventional pan, which involves the simultaneous application of a powder blend with the application of the binder to facilitate adhesion to a seed or inner core acid portion. The incipient beads should be in constant movement to prevent their adhesion to one another. This method is similar to the process of sugar coating in a pan. See e.g., Osal (Ed.), "Remington's Pharmaceutical Sciences, 16th Edition," Mack Publishing Company, Easton Pa. (1980); Lachman et al., "The Theory and Practice of Industrial Pharmacy, Third Edition," Lea & Febiger, Phila., PA (1986).

Figure 3:
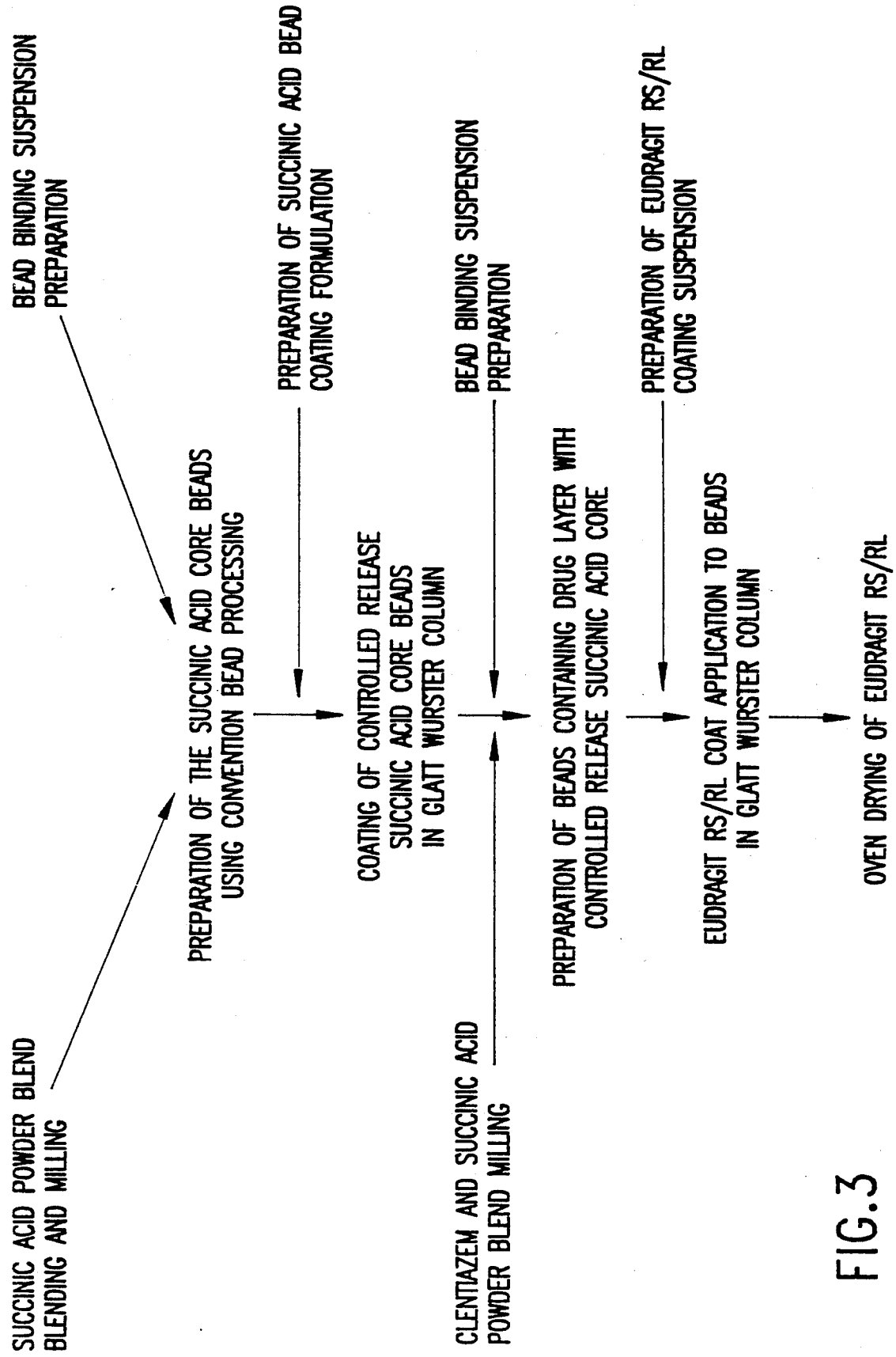
FIG. 3 is a schematic flow-chart of a process for preparing a bead of this invention.

The application of the sustainably-acid-releasing and the sustainably-drug releasing coatings can be by known methods such as film coating in conventional pans or film coating in a fluidized bed suspension coating apparatus. The conventional pan coating process involves application of the coating as a film using the coating substance, say, of a polymer, in a solution or suspension, which is applied to the incipient beads while they are in constant motion. Heat is generally applied to dry the coating. The fluidized bed coating process involves the application of the coating substance, again say, a polymer, in solution or suspension, using a spray nozzle to atomize the coating solution or suspension for application to the incipient beads, which are in motion in the fluidized bed apparatus. Generally, the incipient beads move up a column where the coating is applied and dry in an expansion chamber. This process is cyclic in nature, occurring repeatedly until the desired amount of coating is applied. See e.g., Osal (Ed.), supra; Lackman et al., supra. Preferably, however, preparation of the beads is carried out according to such a scheme as especially indicated in FIG. 3.

Thus, preparations of the beads can be by building up the inner core portion containing alkyl or substituted alkyl carboxylic acid(s), coating this with the sustainably acid-releasing coating, to provide the multi-layered core, then, building upon the multi-layered core the inner periphery of the mixture of at least the pharmaceutical compound(s) and the surface-active agent(s), and coating this with the sustainably drug-releasing coating. Any optional component(s) are added, if desired, at suitable times in the preparation, as is understood in the art. The following more critical features in preferred preparations of preferred beads of this invention are noted:

1. When building the succinic acid core bead using the binder containing white wax, castor oil, and stearic acid, the bed temperatures for the incipient beads should be about from 10 to 16 degrees C, not more than about 20 degrees C.

2. All powders used to build the beads should be milled to an extremely fine particle size, say, on the average at most about 75 microns, 3. During application of powder which contains the drug, the bed temperatures should be about from 15 to 25 degrees C.

4. During application of the sustainably-acid-releasing coating in a fluidized bed coating apparatus, outlet air temperature should be about from 25 to 35 degrees C.

5. During application of the sustainably-drug-releasing coating in a fluidized bed coating apparatus, outlet air temperature should be about from 25 to 35 degrees C.

The beads of this invention can be employed in such formats as, for instance, in capsules, in tablets, in degrees, in syrups, and so forth and the like, which can be prepared with the beads of this invention by known methods. Preferably, the beads are employed in gelatin capsules.

Administration of the controlled release bead(s) can be by orally ingesting a sample thereof. The administration in the practice hereof effects a generally pH independent sustained and controlled release of the pharmaceutical compound(s) contained in the bead(s).

The administration is efficient. Accordingly, the efficient release of the pharmaceutical compound(s) is not only generally independent of pH but is also so typically even at higher pH values. The release profile of the pharmaceutical compound from the beads may be substantially linear. Optionally and advantageously, the release is in a stair-stepped profile which is provided by preparing a suitable blend or mixture of beads having rapid release profiles which follow differing lag times. Beads having differing release lag times can be readily prepared by varying the thickness and/or composition of the sustainably-drug-releasing coating.

The efficient administration hereof allows for dosing of the suitable pharmaceutical compounds on a once-a-day schedule. This, heretofore, was generally problematical if not impossible to effect for many of such compounds.

The patient can be a mammal. The mammal can be a human.

Dosages can be those pharmaceutically useful and will depend on the pharmaceutical compound used. For example, for a benzothiazepine compound such as clentiazem, an appropriate human dose can be selected from among those about from 10 to 160 mg per day, to include from among those about from 20 to 120 mg per day and about from 30 to 80 mg per day.

A once-daily (QD) dosage format is advantageously employed.

The following further illustrates the invention. Parts and percentages therein are by weight, unless specified otherwise.

EXAMPLE 1

A sample of 89.5 parts succinic acid, 10.0 parts talc, and 0.5 parts silicon dioxide was blended, and then milled to a finely divided powder using a conventional milling machine.

A binder composition was prepared by melting 1.73 parts white wax and adding it, along with 3.45 parts ethylcellulose, 1.14 parts castor oil and 0.57 parts stearic acid to 93.11 parts isopropyl alcohol, and mixing this with a conventional mixer.

A sample of 0.8 kg of 35-45 mesh sugar-starch seeds was placed in a standard bead building apparatus and rotation begun. The seeds were sprayed with the binder composition until they became sufficiently adhesive to allow the application of the powder sample above. An amount of 3.2 kg of the powder sample was applied with simultaneous application of 1.8 kg of the binder composition. The bead bed temperature was maintained in the range of 12 to 15 degrees C during the application of the powder and binder. These incipient bead inner core portions were dried for 12 hours in a conventional oven set at 40 degrees C to remove solvent.

A coating composition for the sustainably-acid-releasing coating was prepared from 2.5 parts ethylcellulose, 0.25 parts acetyl tributyl citrate, 0.25 parts HPMC E-15 (SOURCE: Dow Chemical Co.), 1.0 parts talc, 2.0 parts magnesium stearate, and 94.0 parts denatured alcohol.

An amount of 1.5 kg of the dried inner core portions from above were charged into a conventional fluidized bed coating apparatus and were coated with 2.175 kg of the sustainably-acid-releasing coating composition. The incipient multi-layered cores were coated while maintaining an outlet air temperature in the range of 25 to 35 degrees C. The incipient cores were then dried for 12 hours in a conventional oven at 40 degrees C to remove solvent.

A drug-containing powder for the inner portion of the periphery of the beads was prepared by blending 65.23 parts clentiazem, 27.27 parts succinic acid, 5.0 parts talc, 0.5 parts silicon dioxide, and 2.0 parts sodium lauryl sulfate in a conventional blender. The blend was milled to a fine particle size using a conventional milling machine.

Another binder composition was prepared. It contained 2.5 parts HPMC at 15 centipoise (cps), 1.0 parts talc, 10.0 parts water, and 86.5 parts denatured alcohol.

An amount of 1.26 kg of the multi-layered cores above was placed in a conventional bead building apparatus. An amount of the other, latter, binder composition was sprayed on the cores to allow for adhesion of the drug-containing powder. Then 640.9 g of the drug-containing powder along with 524 g of the other, latter, binder composition was applied. The bead bed temperature in the apparatus was maintained in the range of 15 to 25 degrees C during the application of the binder and powder. The incipient beads were dried for 12 hours at 40 degrees C. to remove residual solvent.

Another coating composition, for the sustainably-drug-releasing coating, was prepared from 37.37 parts Eudragit TM 30 D, 1.97 parts Eudragit TM RL 30 D, 2.32 parts acetyl tributyl citrate, 5.70 parts talc, and 52.64 parts water.

An amount of 900 g of the incipient multi-layered beads containing the drug was charged into a conventional fluidized bed coating apparatus. The beads were coated with a sufficient amount of the other, latter, coating composition to result in a bead sample which contained 22.5 percent sustainably-drug-releasing coating solids based on the finished beads. During the latter coating application, the outlet temperature of the coating apparatus was maintained in the range of 25 to 35 degrees C. The beads were dried for 5 minutes in the coating apparatus, then dusted with 2.0 percent talc based on the finished beads, and then dried for 5 days in a conventional oven at 55 degrees C, to provide finished beads suitable for blending with other beads for once a day administration.

The finished beads were dissolution tested as follows:

Apparatus: Type 2 paddle assembly, USP XXII, at 100 rotations per minute (rpm) and 37 degrees C.

Aqueous test solutions: Potassium dihydrogen phosphate buffered pH 7.5, or HCl-KCl pH 1.2, as in USP XXII, at pages 1784-1785.

Figure 4:
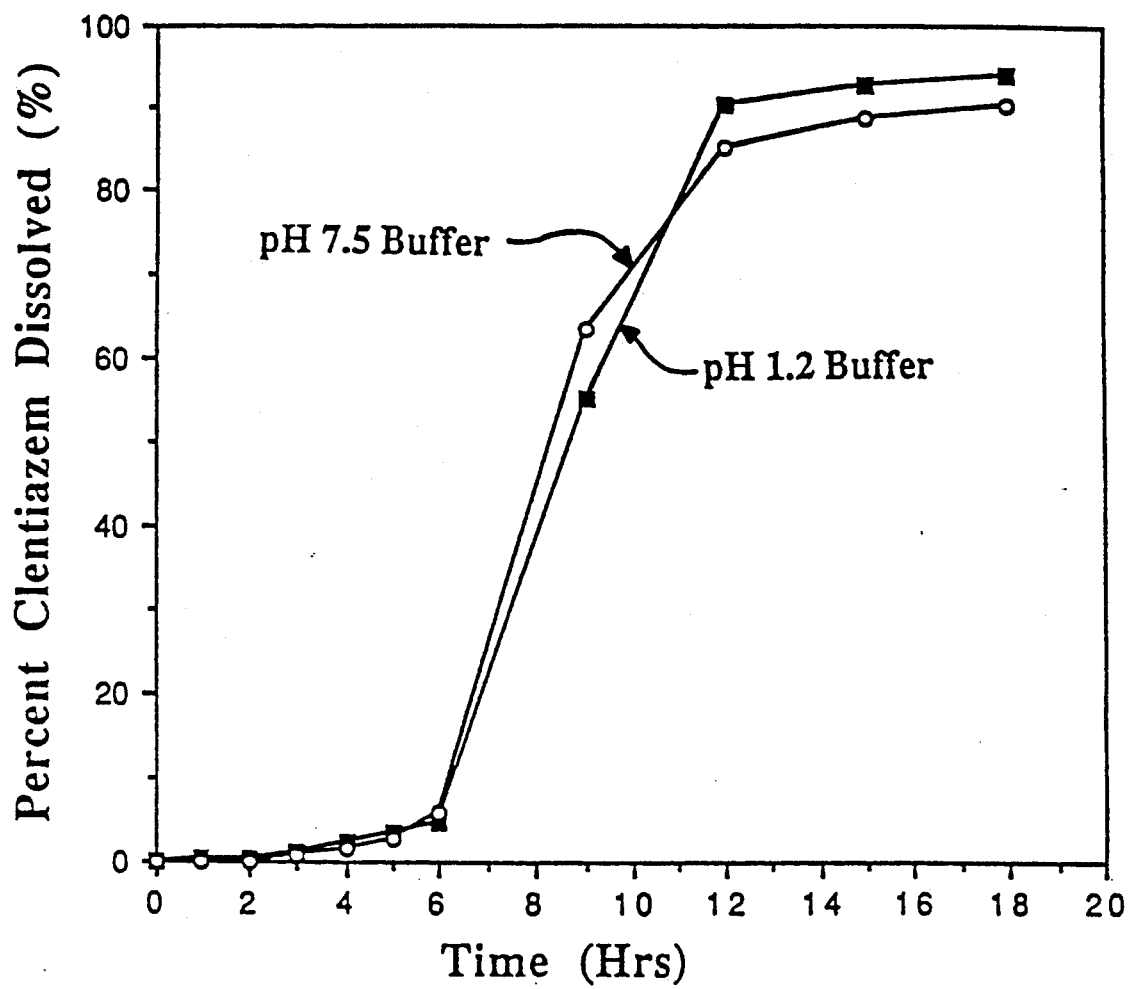
FIG. 4 is a graph of percent of clentiazem dissolved into an aqueous solution on the ordinate versus time in hours on the abscissa, at pH values of 1.2 and 7.5, for 22.5 percent Eudragit TM peripherally-coated beads of this invention, the periphery of which contains clentiazem, succinic acid and sodium lauryl sulfate.

Method: An mount of beads equivalent to 60 mg of clentiazem was placed in each vessel. Upon testing, 4.9 mL samples were withdrawn at one-hour intervals up to 6 hours, then at 3-hour intervals until 18 hours. The samples were measured immediately after removal using a spectrophotometer. The absorbance value equivalent to 100 percent was determined by dissolving 60 mg of a clentiazem reference standard in 900 mL of water, then reading the absorbance. The percentage dissolution was calculated by dividing the sample absorbance reading by the 100 percent absorbance standard reading. Table II lists observed results, which are also presented graphically in FIG. 4.

TABLE II

| Time | Dissolution pH 1.2 | Dissolution pH 7.5 |
| --- | --- | --- |
| 1 hour | 0.3% | 0.0% |
| 2 hours | 0.6% | 0.2% |
| 3 hours | 1.2% | 0.8% |
| 4 hours | 2.5% | 1.6% |
| 5 hours | 3.6% | 2.9% |
| 6 hours | 5.0% | 6.1% |
| 9 hours | 55.0% | 63.6% |
| 12 hours | 90.6% | 85.2% |
| 15 hours | 92.9% | 88.9% |
| 18 hours | 94.0% | 90.3% |

EXAMPLE 2

Succinic acid-containing controlled-release multi-layered inner cores coated with ethylcellulose and HPMC were prepared as described in Example 1, in the parts there said.

A drug-containing powder for the inner portion of the periphery of the beads was prepared by blending 92.5 parts clentiazem, 5.0 parts talc, 0.5 parts silicon dioxide, and 2.0 parts sodium lauryl sulfate in a conventional blender. The blend was milled to a fine particle size using a conventional milling machine.

Another binder composition containing HPMC was prepared as described in Example 1, in the parts there said.

An amount of 1,448 kg of the multi-layered cores was placed in a conventional bead building apparatus. An amount of the other, latter, binder composition was sprayed on the cores to allow for adhesion of the drug-containing powder. Then 452 g of the drug-containing powder along with 474 g of the other, latter, binder composition was applied. The bead bed temperature in the apparatus was maintained in the range of 15 to 25 degrees C during application of the binder and powder. The incipient beads were dried for 12 hours at 40 degrees C to remove residual solvent.

Another coating composition, for the sustainably-drug-releasing coating, was prepared as described in Example 1, in the parts there said.

The incipient multi-layered beads were coated with the sustainably-drug-releasing coating as described in Example 1 to achieve 22.5 percent sustainably-drug-releasing coating on the finished beads. Once the beads were removed from the coating apparatus, they were dusted with 2.0 percent talc based on the finished beads, and then dried for 5 days in a conventional oven at 55 degrees C to provide finished beads suitable for blending with other beads for once a day administration.

The finished beads were dissolution tested as in Example 1.

Figure 5:
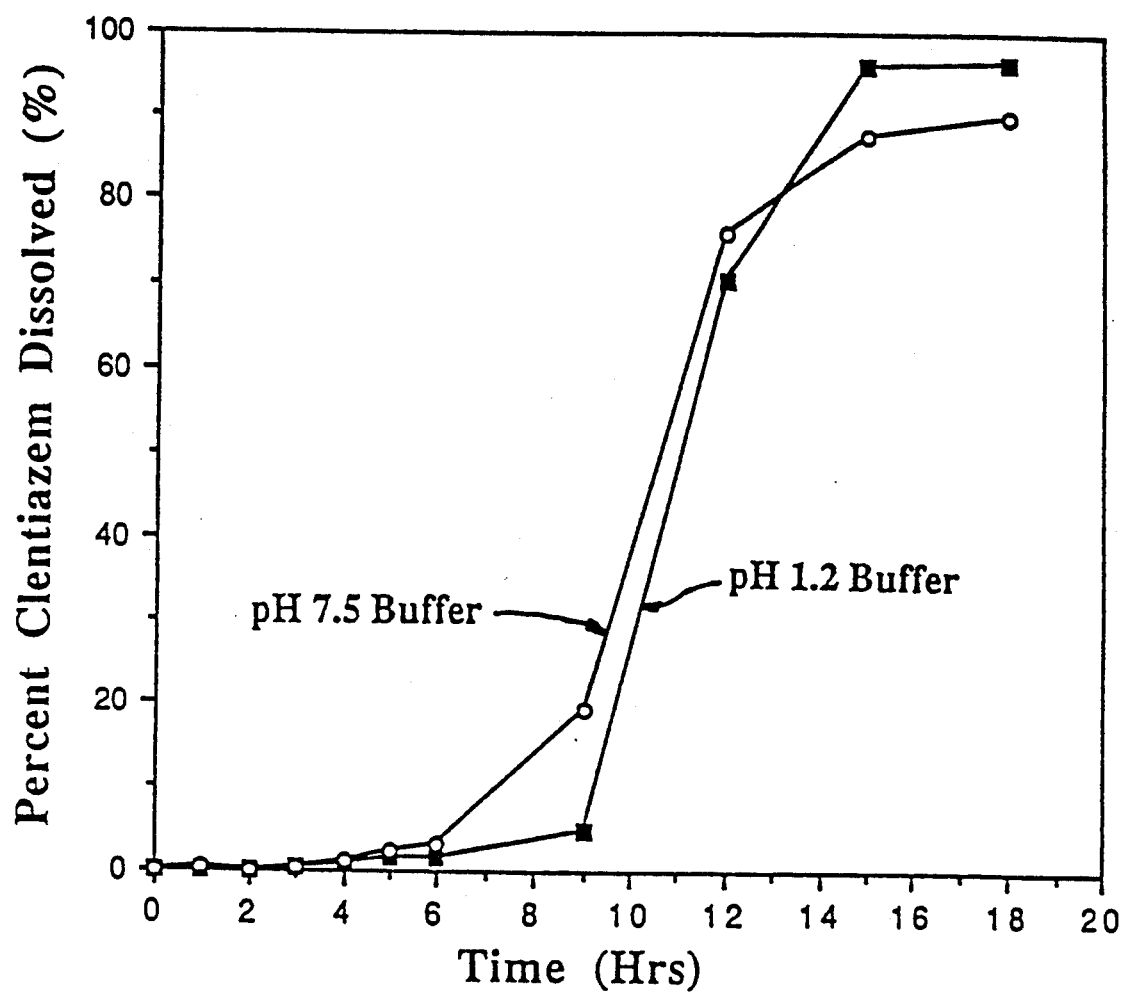
FIG. 5 is a graph of percent of clentiazem dissolved into an aqueous solution on the ordinate versus time in hours on the abscissa, at pH values of 1.2 and 7.5, for 22.5 percent Eudragit TM peripherally-coated beads of this invention, the periphery of which contains clentiazem and sodium lauryl sulfate, but no succinic acid.

Table III lists observed results, which are also presented graphically in FIG. 5.

TABLE III

| Time | Dissolution pH 1.2 | Dissolution pH 7.5 |
| --- | --- | --- |
| 1 hour | 0.0% | 0.3% |
| 2 hours | 0.1% | 0.2% |
| 3 hours | 0.6% | 0.6% |
| 4 hours | 0.9% | 1.3% |
| 5 hours | 1.4% | 2.2% |
| 6 hours | 1.7% | 3.3% |
| 9 hours | 5.0% | 19.0% |
| 12 hours | 70.6% | 76.1% |
| 15 hours | 95.9% | 87.8% |
| 18 hours | 96.2% | 90.1% |

EXAMPLE 3

Incipient multi-layered beads, containing multi-layered core and inner drug-containing periphery, were prepared as described in Example 1 in the parts there said.

Another coating composition, for the sustainably-drug-releasing coating, was prepared. It contained 80.64 parts Aquacoat ® E 30 D (aqueous dispersion of ethylcellulose), 5.8 parts triethyl citrate, and 13.55 parts water.

An amount of 900 g of the incipient multi-layered beads containing the drug was charged into a conventional fluidized bed coating apparatus. The beads were coated with 157.9 g of the other, latter, coating composition to result in a bead sample which contained 5 percent sustainably-drug-releasing coating solids based on the finished beads. During the latter coating application, the outlet temperature of the coating apparatus was maintained in the range of 25 to 35 degrees C. The beads were dried for 5 minutes in the coating apparatus and then dried for 3 hours in a conventional oven at 55 degrees C to provide finished beads suitable for once a day administration.

The finished beads were dissolution tested, as in Example 1. However, only the pH 7.5 test solution was employed.

Figure 6:
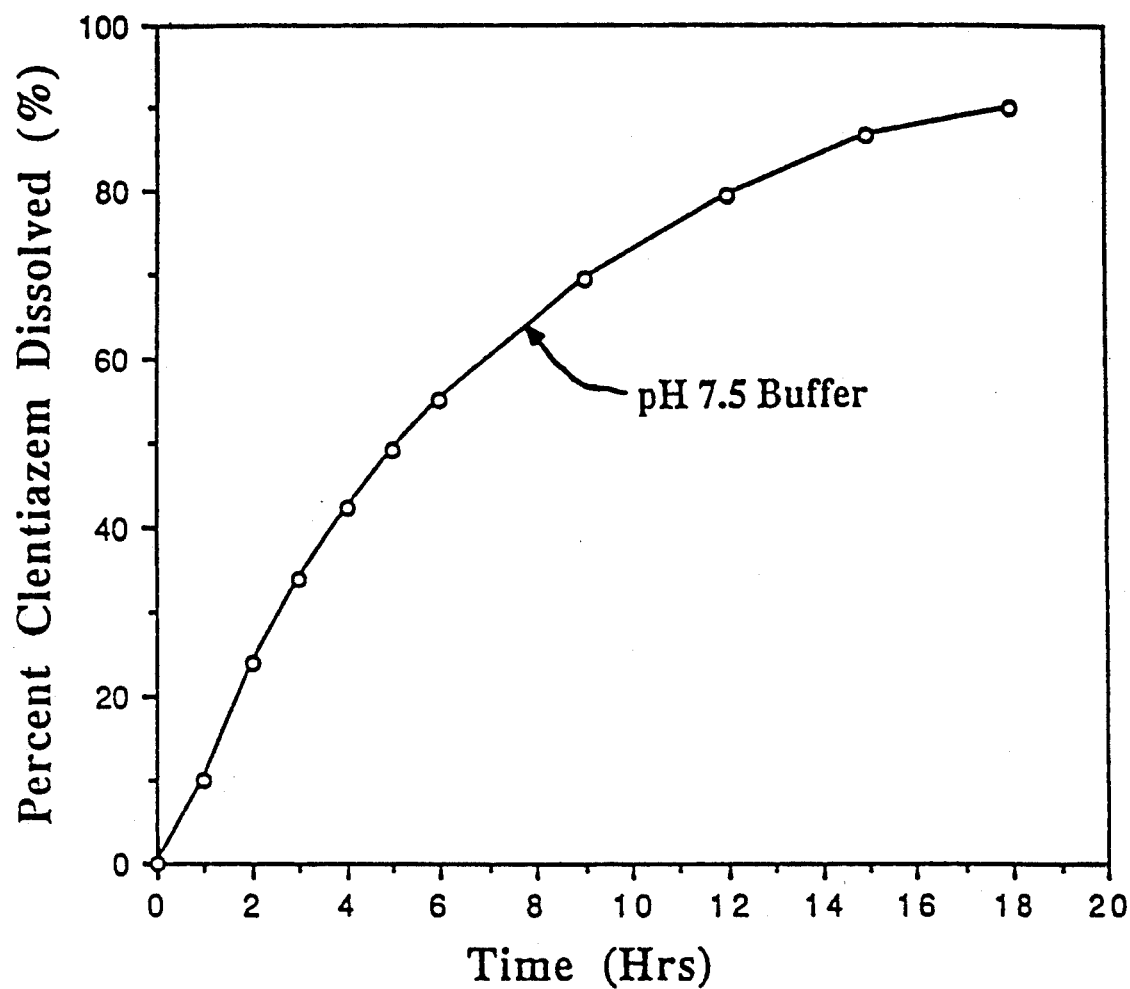
FIG. 6 is a graph of percent of clentiazem dissolved into an aqueous solution on the ordinate versus time in hours on the abscissa, at a pH value of 7.5, for 5 percent Aquacoat ® peripherally-coated beads of this invention, the periphery of which contains clentiazem, succinic acid and sodium lauryl sulfate.

Table IV lists observed results, which are also presented graphically in FIG. 6.

TABLE IV

| Time | Dissolution pH 7.5 |
| --- | --- |
| 1 hour | 9.9% |
| 2 hours | 23.8% |
| 3 hours | 33.9% |
| 4 hours | 42.3% |
| 5 hours | 49.2% |
| 6 hours | 55.3% |
| 9 hours | 69.5% |
| 12 hours | 79.7% |
| 15 hours | 86.7% |
| 18 hours | 90.1% |

EXAMPLE 4

A sample of 94.5 parts succinic acid, 5.0 parts talc, and 0.5 parts silicon dioxide was blended, and then milled to a finely divided powder, using conventional blending and milling machines.

A binder composition was prepared as described in Example 1 with white wax, ethylcellulose, castor oil, stearic acid, and isopropyl alcohol, in the parts there said.

A sample of 1.88 kg of 35–45 mesh sugar-starch seeds was placed in a standard bead building apparatus, and rotation begun. The seeds were sprayed with the binder composition until they became sufficiently adhesive to allow the application of the powder sample above. An amount of 2.122 kg of the powder sample was applied with simultaneous application of 1.064 kg of the binder composition. The bead bed temperature in the apparatus was maintained in the range of 15 to 25 degrees C during application of the binder and powder. The incipient bead inner core portions were dried for 12 hours in a conventional oven set at 40 degrees C to remove residual solvent.

A coating composition for the sustainably-acid-releasing coating was prepared as described in Example 1 with ethylcellulose, acetyl tributyl citrate, HPMC E-15, talc, magnesium stearate, and denatured alcohol, in the parts there said.

An amount of 1.5 kg of the dried inner core portions from above were charged into a conventional fluidized bed coating apparatus and were coated with 2.5783 kg of the sustainably-acid-releasing coating composition. The incipient multi-layered cores were coated while maintaining an outlet air temperature in the range of 30 to 35 degrees C. The incipient cores were then dried for 12 hours at 50 degrees C to remove solvent.

A drug-containing powder for the inner portion of the periphery of the beads was prepared as described in Example 1 with clentiazem succinic acid, talc, silicon dioxide, and sodium lauryl sulfate in the parts there said.

Another binder composition was prepared as described in Example 1 with HPMC at 15 cps, talc, water, and denatured alcohol in the parts there said.

An amount of 488.2 g of the multi-layered cores above was placed in a conventional bead building apparatus. An amount of the other, latter, binder composition was sprayed on the cores to allow for adhesion of the drug-containing powder. Then 1.0118 kg of the drug-containing powder along with 623 g of the other, latter, binder composition was applied. The bead bed temperature was maintained in the range of 15 to 25 degrees C in the apparatus during the application of the binder and powder. The incipient beads were dried for 12 hours at 50 degrees C to remove residual solvent.

Another coating composition, for the sustainably-drug-releasing coating, was prepared as described in Example 1 with Eudragit TM RS 30 D, Eudragit TM RL 30 D, acetyl tributyl titrate, talc, and water, in the parts there said.

An amount of 1.3 kg of the incipient multi-layered beads containing the drug was charged into a conventional fluidized bed coating apparatus. The beads were coated with a sufficient amount of the other, latter, coating composition to result in a bead sample which contained 23.0 percent sustainably-drug-releasing coating solids based on the finished beads. During the latter coating application, the outlet temperature of the coating apparatus was maintained in the range of 25 to 35 degrees C. The beads were dried for 20 minutes in the coating apparatus, then dusted with 2.0 percent talc based on the finished beads, and then dried for five days in a conventional oven at 50 degrees C to provide finished beads suitable for blending with other beads for once a day administration.

The finished beads were dissolution tested as in Example 1.

Figure 7:
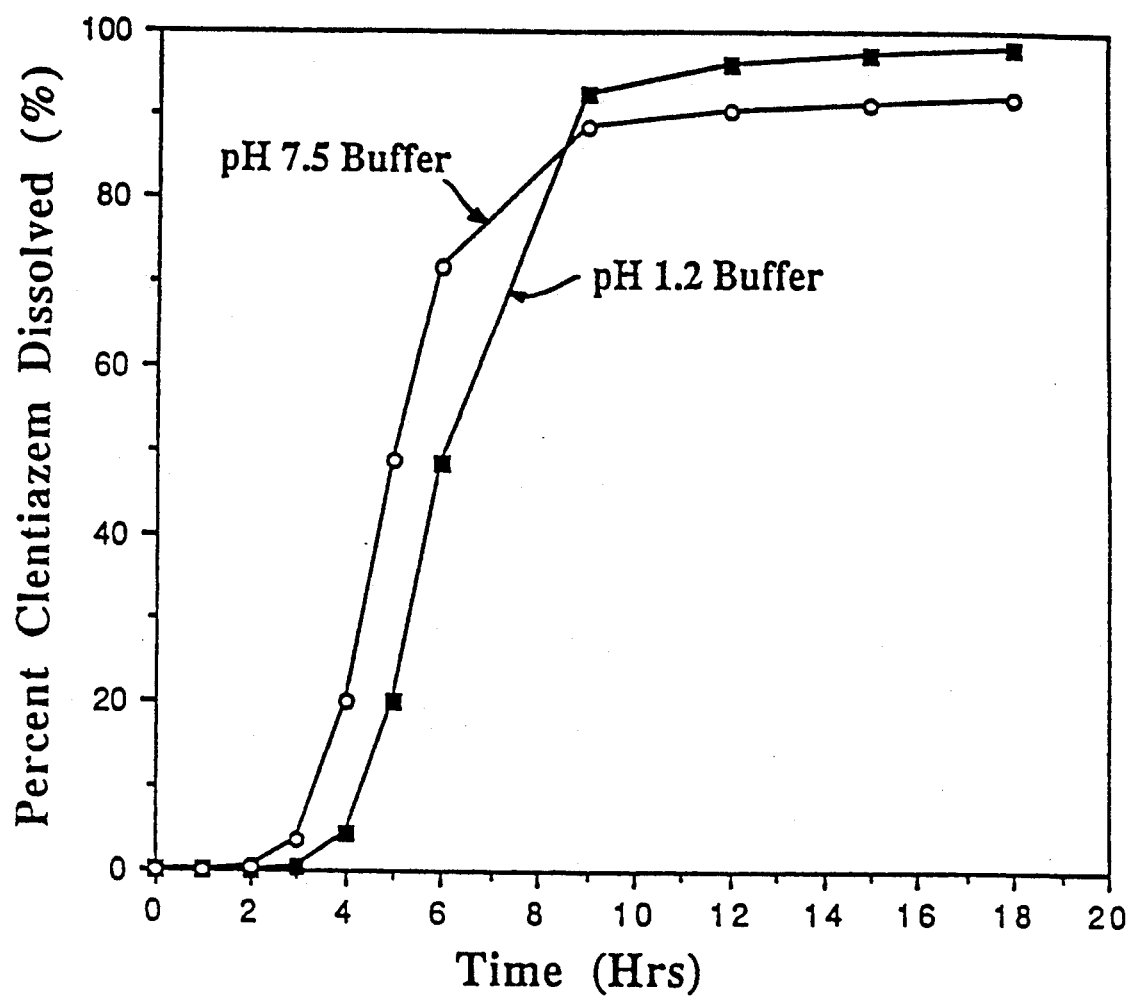
FIG. 7 is a graph of percent of clentiazem dissolved into an aqueous solution on the ordinate versus time in hours on the abscissa, at pH values of 1.2 and 7.5, for 23 percent Eudragit TM peripherally-coated beads of this invention, the periphery of which contains clentiazem, succinic acid and sodium lauryl sulfate.

Table V lists observed results which are also presented graphically in FIG. 7.

TABLE V

| Time | Dissolution pH 1.2 | Dissolution pH 7.5 |
| --- | --- | --- |
| 1 hour | 0.1% | 0.0% |
| 2 hours | 0.1% | 0.3% |
| 3 hours | 0.6% | 3.7% |
| 4 hours | 4.5% | 20.1% |
| 5 hours | 20.2% | 48.8% |
| 6 hours | 48.4% | 71.5% |
| 9 hours | 92.5% | 88.2% |
| 12 hours | 96.1% | 90.3% |
| 15 hours | 97.2% | 91.1% |
| 18 hours | 98.1% | 91.9% |

EXAMPLE 5

A drug containing powder for the inner portion of the periphery of the beads is prepared by blending 58.87 parts noscapine, 33.63 parts succinic acid (a 2:1 molar ratio of noscapine to succinic acid), 5.0 parts talc, 0.5 parts silicon dioxide and 2.0 parts sodium lauryl sulfate in a conventional blender. The blend is then milled to a fine particle size using a conventional milling machine.

Finished beads are prepared as in Example 1 with the noscapine containing powder described above being substituted for the powder described in Example 1. All other parameters and conditions remain the same.

The finished beads are tested as described in Example 1 using an appropriate amount of beads to yield an acceptable absorbance as determined by a spectrophotometer.

EXAMPLE 6

A drug containing powder for the inner portion of the periphery of the beads is prepared by blending 40.02 parts theophylline, 52.48 parts succinic acid (2:1 molar ratio of succinic acid to theophylline), 5.0 parts talc, 0.5 parts silicon dioxide and 2.0 parts sodium lauryl sulfate in a conventional blender. The blend is milled to a fine particle size using a conventional milling machine.

Finished beads are prepared as in Example 1 with the theophylline containing powder being substituted for the powder described in Example 1. All other parameters and conditions remain the same.

The finished beads are tested as described in Example 1 using an appropriate amount of beads to yield an acceptable absorbance as determined by a spectrophotometer.

EXAMPLE 7

A drug containing powder for the inner portion of the periphery of the beads is prepared by blending 51.58 parts hydrochlorothiazide, 40.92 parts succinic acid (2:1 molar ratio of succinic acid to hydrochlorothiazide), 5.0 parts talc, 0.5 parts silicon dioxide and 2.0 parts sodium lauryl sulfate in a conventional blender. The bend is then milled to a fine particle size using a conventional milling machine.

Finished beads are prepared as in Example 1 with the hydrochlorothiazide containing powder described above being substituted for the powder described in Example 1. All other parameters and conditions remain the same.

The finished beads are tested as described in Example 1 using an appropriate amount of beads to yield an acceptable absorbance as determined by a spectrophotometer.

17

EXAMPLE 8

A drug containing powder for the inner portion of the periphery of the beads is prepared by blending 51.71 parts codeine, 40.79 parts succinic acid (2:1 molar ratio of guccitic acid to codeine), 5.0 parts talc, 0.5 parts silicon dioxide and 2.0 parts sodium lauryl sulfate in a conventional blender. The blend is then milled to a fine particle size using a conventional milling machine.

Finished beads are prepared as in Example 1 with the codeine containing powder described above being substituted for the powder described in Example 1. All other parameters and conditions remain the same.

The finished beads are tested as described in Example 1 using an appropriate amount of beads to yield an acceptable absorbance as determined by a spectrophotometer.

EXAMPLE 9

A sample of 89.5 parts maleic acid, 10.0 parts talc, and 0.5 parts silicon dioxide are blended and then milled to a finely divided powder using a conventional milling machine.

A binder is prepared as in Example 1.

A sample of 0.8 kg of 35-45 mesh sugar-starch seeds is placed in a standard bead building apparatus and rotation is started. The seeds are sprayed with the binder composition until they become sufficiently adhesive to allow application of the powder sample described above. An amount of 3.2 kg of the powder sample is applied with simultaneous application of approximately 1.8 kg of the binder composition. These incipient bead inner core portions are allowed to dry at 40 degrees C for 12 hours in a conventional oven.

A sustainably-acid-releasing coating is prepared and applied as described in Example 1.

A drug containing powder for the inner portion of the periphery of the beads is prepared by blending 65.23 parts clentiazem, 27.27 parts maleic acid, 5.0 parts talc, 0.5 parts silicon dioxide, and 2.0 parts sodium lauryl sulfate in a conventional blender. The blend is milled to a fine particle size using a conventional milling machine.

A binder containing HPMC is prepared as described in Example 1.

An amount of 1.26 kg of the multi-layered cores containing maleic acid are placed in a conventional bead building apparatus. An amount of the HPMC containing binder composition is sprayed on the cores to allow for adhesion of the drug-containing powder. Then 640.9 g of the drug-containing powder along with approximately 524 g of the HPMC containing binder composition are applied to the core. The incipient beads are allowed to dry for 12 hours at 40 degrees C to remove residual solvent.

The sustainably-drug-releasing coating is prepared and applied to the beads as described in Example 1.

The resulting beads are tested as described in Example 1.

EXAMPLE 10

The inner core portion of the bead is prepared and a sustainably-acid-releasing core is prepared and applied, all as described in Example 1.

A drug containing powder for the inner portion of the periphery of the beads is prepared by blending 65.23 parts clentiazem, 27.27 parts succinic acid, 5.0 parts talc, 0.5 parts silicon dioxide and 2.0 parts calcium stearoyl-2-lactylate in a conventional blender. The blend is milled to a fine particle size using a conventional milling machine. A water cooled jacketed mill head may be used to prevent melting of the powder during milling.

A binder containing HPMC is prepared as described in Example 1.

A drug containing multilayered bead is prepared as described in Example 1 using the drug containing powder described above and the sustainably-drug-releasing coating of Example 1. All other parameters and conditions remain the same.

Testing of the finished beads is carried out as described in Example 1.

EXAMPLE 11

Conventional Bead Biostudy Data

A sample of 35.37 parts clentiazem, 59.13 parts succinic acid, 5.00 parts talc and 0.5 parts silicon dioxide was blended in a conventional powder blender, and then milled to a finely divided powder using a conventional milling machine.

A binder was prepared by dissolving 2.0 parts hydroxypropyl methylcellulose and 2.0 parts Povidone in 80.0 parts denatured alcohol and 12 parts water. Then 4.0 parts talc was added to the solution.

A sample of 15.6 kg of 25-30 mesh sugar-starch seeds was placed in a standard bead building apparatus and rotation begun. The seeds were sprayed with the binder solution prepared above until they became sufficiently adhesive to allow the application of the powder blend prepared above. A quantity of 23.4 kg of the powder was applied with the simultaneous application of 6,865 kg of the binder solution. This powder application process was conducted with the bead bed temperature ranging between 11 and 15 degrees C. These instant release beads were dried for 12 hours in a conventional oven set at 40 degrees C to remove any remaining solvent.

A sustained release coating composition was prepared with 39.00 parts Eudragit RS 30 D, 1.15 parts triethyl citrate, 5.7 parts talc and 54.15 parts water using a conventional liquid mixer. The suspension was allowed to stand for 24 hours before use.

A quantity of 5.000 kg of the drug containing beads prepared above was charged into a conventional fluidized bed coating apparatus. The beads were coated with a sufficient amount of sustained release coating, from above to yield beads with a 13.0% w/w coating. During this coating operation, the outlet temperature of the coating apparatus was maintained in the range of 22 to 30 degrees C. The beads were dried for 5 minutes in the coating apparatus, then mixed with 2.00 percent talc based on the finished bead weight. The beads were placed on trays and dried in a conventional oven set at 55 degrees C for 5 days.

A separate sample of the drug containing beads, from above (3.000 kg) was charged into a conventional fluidized bed coating apparatus. The beads were coated with a sufficient amount of sustained release coating, from above to yield beads with a 22.5% w/w coating. During this coating operation the outlet temperature of the coating apparatus was maintained in the range of 22 to 30 degrees C. The beads were dried for 5 minutes in the coating apparatus, then mixed with 2.00 percent talc based on the finished bead weight. The beads were placed on trays and dried in a conventional oven set at 55 degrees C for 5 days.

The sustained release coated beads from above were screened over a 30 mesh screen to remove the excess talc. A blend of the beads was then prepared by mixing 48.37 parts of the beads with a 13% sustained release coating and 51.63 parts of the beads containing a 22.5% sustained release coating, in a conventional blender. The blend of beads was filled into gelatin capsules on a conventional capsule filling machine that used a volumetric dosator fill mechanism. The capsules were filled with an amount of beads such that the filled capsules would contain 60 mg of the clentiazem. The weight of fill was determined based on the drug potency of the bead blend.

The finished capsules were tested as follows:

Apparatus: Type 2 paddle assembly, USP XXII, at 100 rotations per minute (RPM) and 37 degrees C.

Aqueous test solutions: Potassium dihydrogen phosphate buffer to pH 7.5, or HCL-KCL pH 1.2, as in USP XXII, pages 1784–1785.

Figure 8:
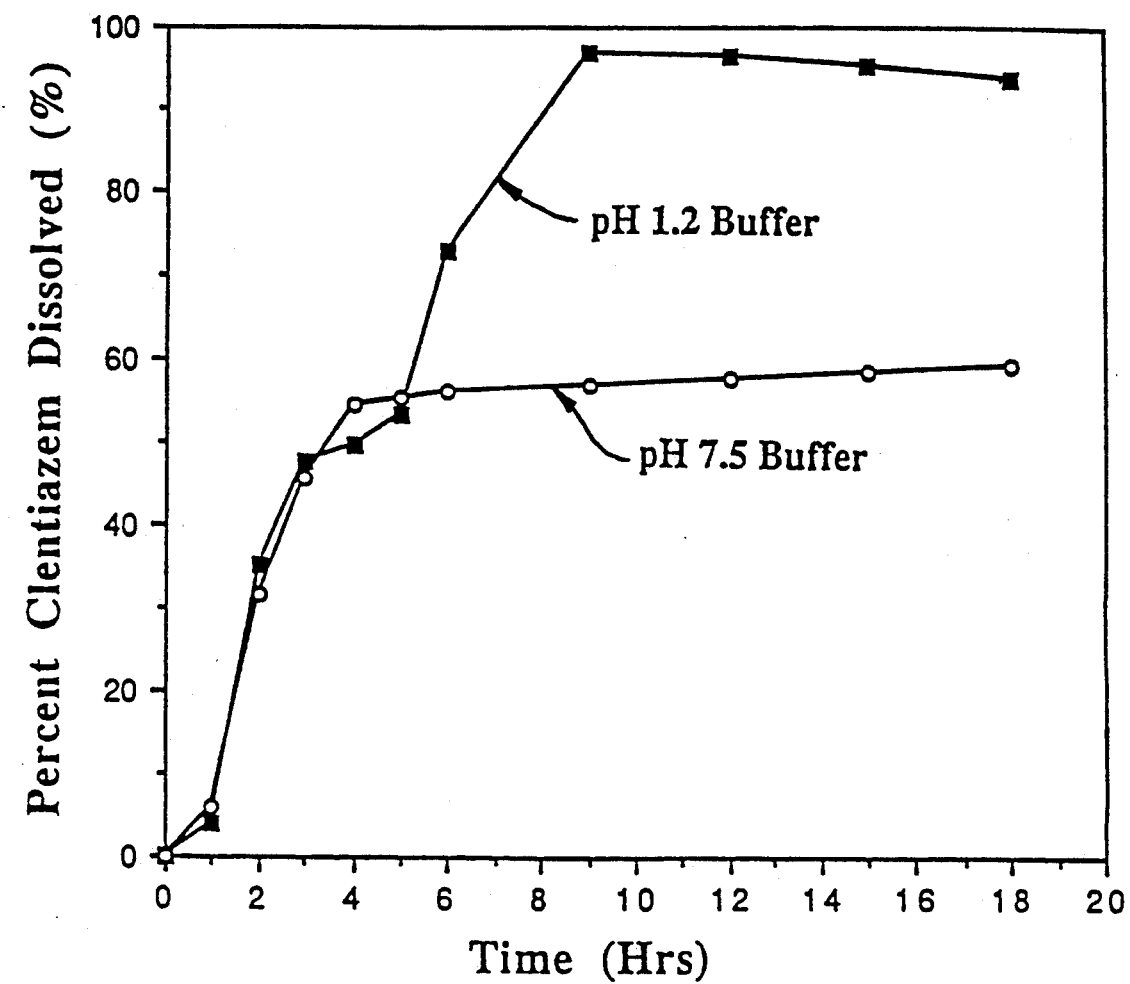
FIG. 8 is a graph of percent of clentiazem dissolved into an aqueous solution on the ordinate versus time in hours on the abscissa, at pH values of 1.2 and 7.5, for 60 mg capsules filled with a conventional bead formulation coated with Eudragit TM.

Method: One 60 mg clentiazem capsule from above was placed in each vessel. Upon testing, 4.9 mL samples were withdrawn at one-hour intervals up to 6 hours, then at three-hour intervals until 18 hours. The samples were measured for clentiazem concentration as described in Example 1. Table VI lists the observed results, which are also presented graphically in FIG. 8.

TABLE VI

| Time | Dissolution pH 1.2 | Dissolution pH 7.5 |
| --- | --- | --- |
| 1 hour | 3.9% | 6.0% |
| 2 hours | 35.4% | 31.6% |
| 3 hours | 47.6% | 45.8% |
| 4 hours | 49.6% | 54.3% |
| 5 hours | 53.3% | 55.3% |
| 6 hours | 73.0% | 55.8% |
| 9 hours | 96.9% | 56.7% |
| 12 hours | 96.4% | 57.5% |
| 15 hours | 95.4% | 58.4% |
| 18 hours | 93.8% | 59.0% |

A study was conducted with the clentiazem capsules described above and five additional capsule formulations of similar composition to determine the in vivo pharmacokinetics of clentiazem from the sustained release capsule formulations when tested in human subjects. The study consisted of twenty-eight healthy male volunteers between the ages of 19 and 45 years, who participated in the randomized, four-way incomplete block crossover study design. Clentiazem was administered as 60 mg capsules for 7 doses of the sustained release formulations and an oral solution was used as reference given as 30 mg doses twice a day for 7 days.

Blood (plasma) samples were collected just prior to the first dose. Additional samples were obtained following the multiple oral doses as follows:

For the oral solution (reference)—just prior to the 11th dose, just prior to the 13th dose and 1, 2, 3, 4, 6, 8, 10, and 12 hours following the 13th dose and 1, 2, 3, 4, 6, 8, 10, and 12 hours after the 14th dose.

For the sustained release capsules formulations—just prior to the 6th dose, just prior to the 7th dose and 2, 4, 6, 8, 10, 12, 15, 18, 21, and 24 hours after the 7th dose.

Figure 9:
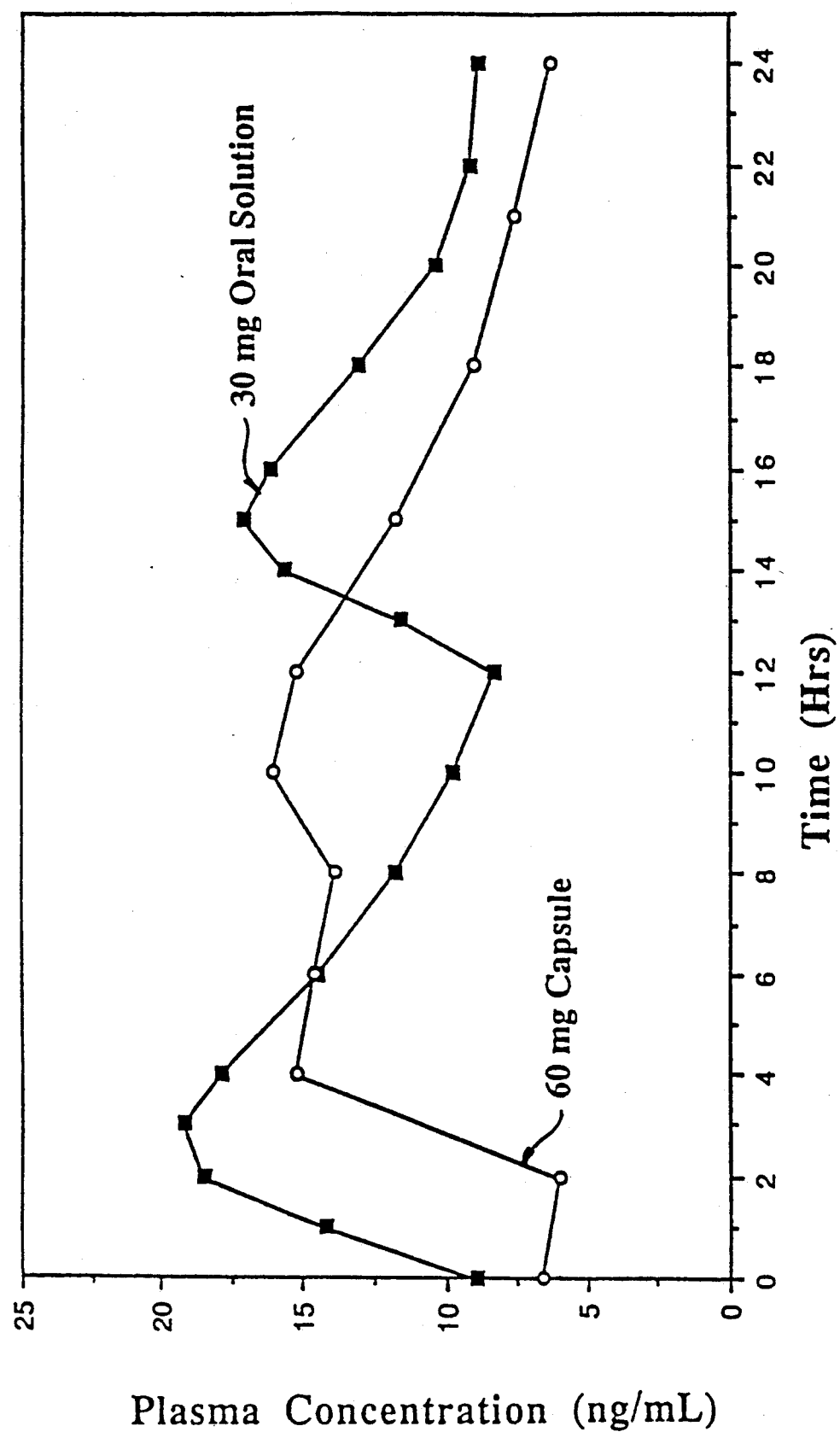
FIG. 9 is a graph of human plasma concentration of clentiazem on the ordinate versus time in hours on the abscissa for 60 mg capsules of a conventional bead formulation coated with Eudragit TM compared to an oral solution of clentiazem.

Plasma concentrations of the clentiazem were determined by HPLC analysis. Model-independent pharmacokinetic data analysis was performed on the resultant clentiazem plasma concentration—time data. The plasma concentration time data for the oral solution and for the sustained release capsule formulation is listed in Table VII. The data listed is a mean of 16 subjects. FIG. 9 is a plot of the clentiazem plasma concentration—time profile for the oral solution and the sustained release capsule formulation described above for the 24 hours on day 7 of treatment.

TABLE VII

| Time | Plasma Concentration (ng/ml) (Oral Solution) 30 mg/BID | Time | Plasma Concentration (ng/mL) (QD Capsule) 60 mg QD |
| --- | --- | --- | --- |
| 13th dose | 8.95 | 7th dose | 6.60 |
| 1 | 14.25 | 2 | 6.03 |
| 2 | 18.49 | 4 | 15.26 |
| 3 | 19.22 | 6 | 14.68 |
| 4 | 17.91 | 8 | 13.93 |
| 6 | 14.53 | 10 | 16.08 |
| 8 | 11.82 | 12 | 15.27 |
| 10 | 9.75 | 15 | 11.76 |
| 12 (14th dose) | 8.36 | 18 | 9.0 |
| 13 | 11.57 | 21 | 7.62 |
| 14 | 15.66 | 24 | 6.35 |
| 15 | 17.05 | | |
| 16 | 16.12 | | |
| 18 | 13.09 | | |
| 20 | 10.40 | | |
| 22 | 9.18 | | |
| 24 | 8.88 | | |

The Mean values for the following pharmacokinetic parameters were determined from the plasma concentration time profiles: AUC=Area under the curve, Cmax=Maximum plasma concentration, Cmin=minimum plasma concentration, Ratio=ratio of C-max to C-rain, Truax=time to maximum concentration, and F=relative bioavailability as compared to the oral solution reference. The mean values for the oral solution and the sustained release clentiazem capsules described above are listed in Table VIII.

TABLE VIII

| Pharmacokinetic Parameter (LS Means) | Oral Solution | SR Capsule |
| --- | --- | --- |
| AUC | 307.31 ng.hr/mL | 278.14 ng.hr/mL |
| CMax | 20.03 ng/mL | 17.95 ng/mL |
| Cmin | 7.84 ng/mL | 6.04 ng/mL |
| Ratio | 2.79 | 3.18 |
| Tmax | 2.68 hours | 8.03 hours |
| F | 1.0 | 0.90 |

The sustained release capsule formulation containing conventional SR beads, which was described above, and all the other similar formulations tested in this human trial were not considered to be once a day formulations. Formulations either exhibited relative bioavailability less than 85% or had trough values which were more than 20% less than those obtained with the reference formulation. The formulation described above was the best among the ones tested, but the minimum concentrations were 22% below the reference treatment.

EXAMPLE 12

Bioavailability Study with Formulation of Invention

A finely divided powder containing succinic acid, talc and silicon dioxide was prepared as described in example 4. A binder composition was prepared as described in Example 1 with white wax, ethylcellulose, castor oil, stearic acid and isopropyl alcohol.

A sample of 1.844 kg of 35–45 mesh sugar-starch seeds was placed in a standard bead building apparatus, and rotation begun. The seeds were sprayed with the binder composition until they became sufficiently adhesive to allow the application of the powder sample above. A quantity of 2.084 kg of the powder sample was applied with the simultaneous application of 1.346 kg of the binder composition. The bead bed temperature in the coating apparatus was maintained in the range of 12–16 degrees C. The beads were dried for 12 hours in a conventional oven set at 50 degrees C to remove residual solvent.

A coating composition for the sustainably-acid releasing coating was prepared as described in Example 1 with ethylcellulose, ATBC, HPMC E-15, talc, magnesium stearate and denatured alcohol.

An amount of 3.626 kg of the dried inner core portions from above were charged into a conventional fluidized bed coating apparatus and were coated with 6.233 kg of the sustainably-acid-releasing coating composition. The inner core portion beads were coated while maintaining an outlet air temperature in the range of 30–35 degrees C. The coated beads were then dried for 12 hours at 50 degrees C in a conventional oven to remove the residual solvent.

A drug containing powder for the inner portion of the periphery of the beads was prepared as described in Example 1 with clentiazem, succinic acid, talc, silicon dioxide and sodium lauryl sulfate.

Another binder composition was prepared as described in Example 1 with HPMC at 15 cps, talc, water and denatured alcohol.

An amount of 1.668 kg of the multi-layered cores from above was placed in a conventional bead building apparatus. An amount of the HPMC containing binder was sprayed on the cores to allow for adhesion of the drug-containing powder. A quantity of 3.457 kg of the drug-containing powder along with 1.543 kg of the binder was applied. The bead bed temperature in the apparatus was maintained in the range of 14–22 degrees C. The beads were dried for 10 minutes in the bead building apparatus and then dried in a conventional oven set at 50 degrees C. for 12 hours to remove any residual solvent. The dried beads were then screened through a 16 mesh and 30 mesh screen. The beads retained on the 16 mesh screen and those passing the 30 mesh screen were discarded. A second batch of drug containing beads was prepared in a similar manor except that 1.283 kg of the multi-layer cores from above was used with 2.66 kg of the drug-containing powder and 1.134 kg of the HPMC containing binder solution from above.

Another coating composition, for the sustainably-drug-releasing coating, was prepared as described in Example 1 with Dudragit RS, RL, ATBC, talc and water.

An amount of 4.423 kg of the drug containing multi-layered beads in the sieve range of 16–30 mesh from above was charged into a conventional fluidized bead coating apparatus. The beads were coated with a sufficient amount of the sustainably-drug-releasing coating to result in a bead sample which contained 11.5% SDR coating solids based on the finished bead weight. During the coating application, the outlet temperature of the coating apparatus was maintained in the range of 20 to 28 degrees C. The beads were dried for 20 minutes in the coating apparatus, removed and mixed with 2.0% talc based on the finished beads. The beads were then dried for 5 days in a conventional oven set at 50 degrees C to provide finished beads suitable for blending with other beads for once-a-day administration.

An amount of 3.406 kg of the drug containing multi-layered beads in the sieve range of 16–30 mesh from above was charged into a conventional fluidized bead coating apparatus. The beads were coated with a sufficient amount of the sustainable-drug-releasing coating to result in a bead sample which contained 21.0% SDR coating solids based on the finished bead weight. During the coating application, the outlet temperature of the coating apparatus was maintained in the range of 20 to 28 degrees. C. The beads were dried for 20 minutes in the coating apparatus, removed and mixed with 2.0% talc based on the finished beads. The beads were then dried for 5 days in a conventional oven set at 50 degrees C to provide finished beads suitable for blending with other beads for once-a-day administration.

The sustained release coated beads from above were screened over a 30 mesh screen to remove the excess talc. A blend of the beads was then prepared by mixing 18.12 parts of the beads with a 11.5% sustained release coating and 81.88 parts of the beads containing a 21.0% sustained release coating, in a conventional blander. The blend of beads was filled into gelatin capsules on a conventional capsule filling machine that used a volumetric dosator fill mechanism. The capsules were filled with an amount of beads such that the filled capsules would contain 60 mg of the clentiazem drug. The weight of fill was determined based on the drug potency of the bead blend.

The finished capsules were tested as follows:

Apparatus: Type 2 paddle assembly, USP XXII, at 100 rotations per minute (RPM) and 37 degrees C.

Aqueous test solutions: Potassium dihydrogen phosphate buffer to pH 7.5, or HCl-KCl pH 1.2, as in USP XXII, pages 1784–1785.

Figure 10:
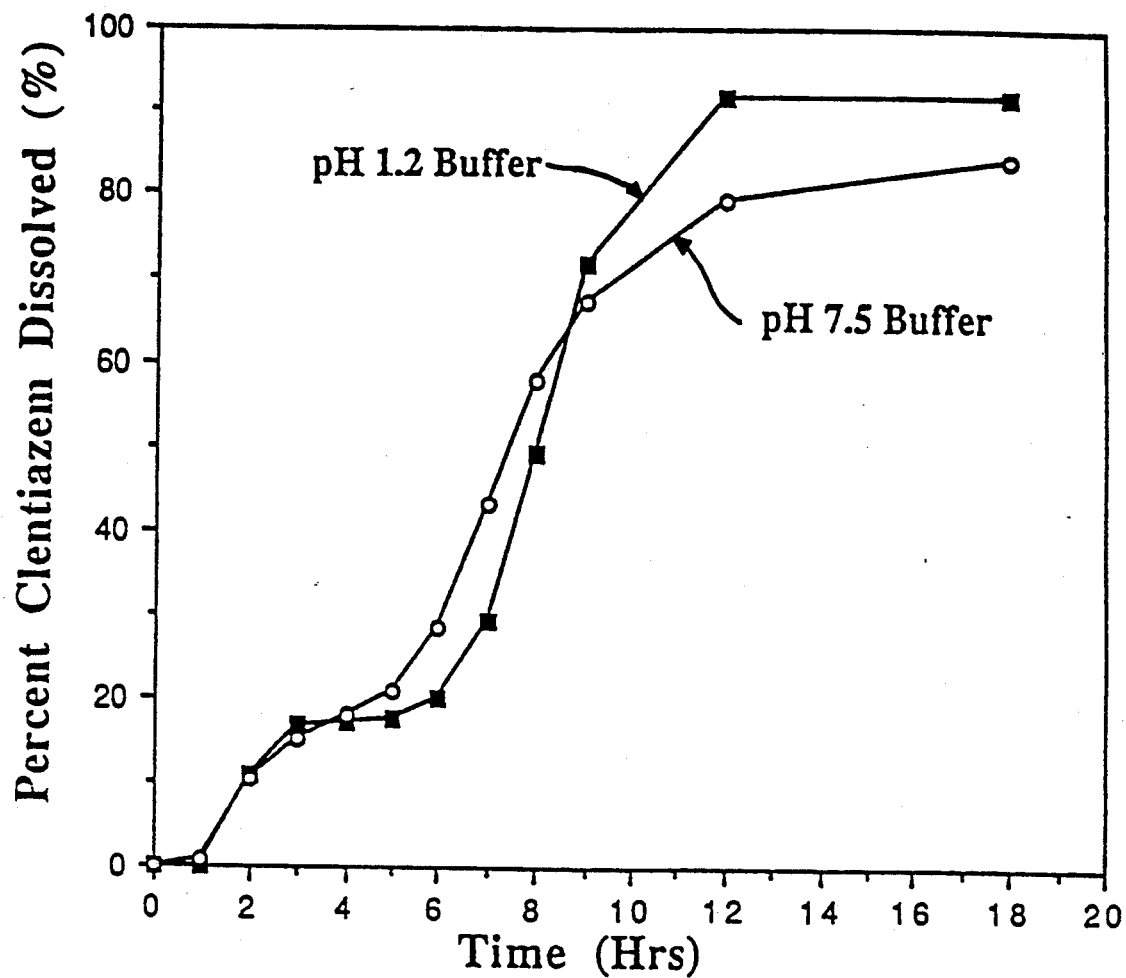
FIG. 10 is a graph of percent of clentiazem dissolved into an aqueous solution on the ordinate versus time in hours on the abscissa, at pH values of 1.2 and 7.5, for 60 mg clentiazem capsules filed with a blend of beads made in accordance with the present invention and coated with 11.5 percent and 21.0 percent Eudragit TM coat.

Methods: One 60 mg clentiazem capsule from above was placed in each vessel. Upon testing, 4.9 mL samples were withdrawn at one-hour intervals up to 9 hours, then at 12 and 18 hours. The samples were measured for clentiazem concentration as described in Example 1. Table IX lists the observed results, which are also presented graphically in FIG. 10.

TABLE IX

| Time | Dissolution pH 1.2 | Dissolution pH 7.5 |
|---|---|---|
| 1 hour | 0% | 0.7% |
| 2 hours | 10.8% | 10.4% |
| 3 hours | 16.7% | 15.3% |
| 4 hours | 17.2% | 18.2% |
| 5 hours | 17.7% | 20.9% |
| 6 hours | 19.9% | 28.5% |
| 7 hours | 29.2% | 43.0% |
| 8 hours | 49.4% | 58.0% |
| 9 hours | 71.5% | 67.2% |
| 12 hours | 91.7% | 79.1% |
| 18 hours | 91.7% | 83.9% |

A study was conducted with the clentiazem capsules described above and five additional capsule formulations of similar composition to determine the relative bioavailability of the clentiazem from the sustained release capsule formulations when tested in human subjects. The study consisted of twenty-eight healthy male volunteers between the ages of 19 and 45 years who participated in the randomized incomplete Latin square study design. Clentiazem was administered as 60 mg capsules for 7 doses of the sustained release formulations and a fast releasing tablet formulation was used as reference given as 30 mg dose twice a day for 7 days. As earlier study showed the tablets to be bioavailable as compared to an oral solution of the clentiazem when tested in humans.

Blood (plasma) samples were collected just prior to the first dose. Additional samples were obtained following the multiple oral doses as follows:

For the tablet reference—just prior to the 13th dose and 1, 2, 3, 4, 6, 8, 10, and 12 hours following the 13th dose and 1, 2, 3, 4, 6, 8, 10, and 12 after the 14th dose.

For the sustained release capsule formulations—just prior to the 7th dose and 2, 4, 6, 8, 10, 12, 15, 18, 21, and 24 hours after the 7th dose. Trough plasma samples were collected prior to the morning dose on day 6 for both formulations.

Figure 11:
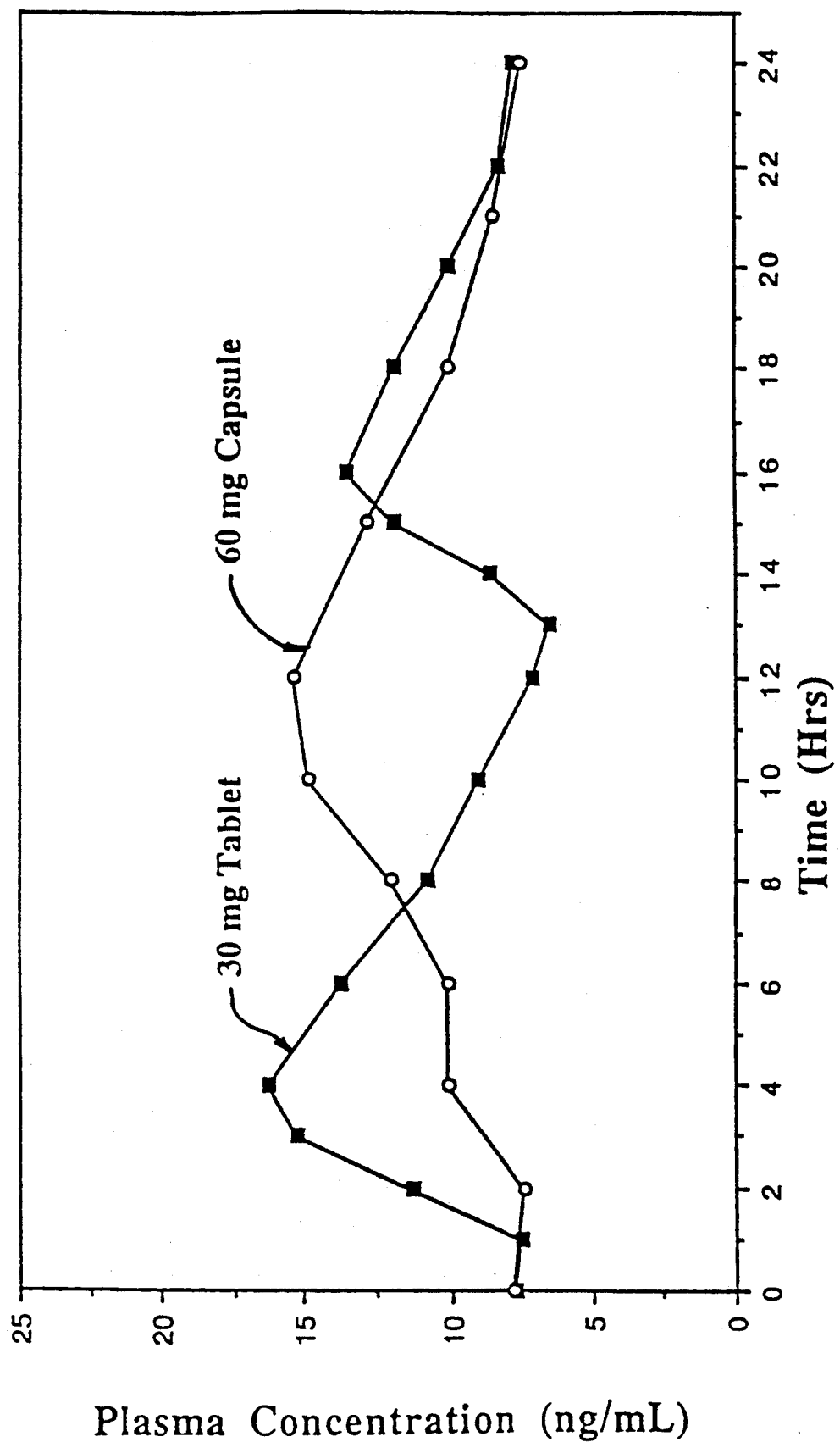
FIG. 11 is a graph of human plasma concentration of clentizem on the ordinate versus time in hours on the abscissa for 60 mg capsules filled with beads made in accordance with the present invention and coated with 1.5 percent and 21.0 percent Eudragit TM coat.

Plasma concentrations of the clentiazem were determined by the HPLC analysis. Model-independent pharmacokinetic data analysis was performed on the resultant clentiazem plasma concentration—time data. The plasma concentration time data for the tablets and the sustained-release capsule formulation described above are listed in Table X. The data listed is a means of 16 subjects. FIG. 11 is a plot of the clentiazem plasma concentration—time profile for the tablet and the sustained release capsule formulation described above of the 24 hours on day 7 of treatment.

TABLE X

| Time | Plasma Concentration (ng/ml) (Oral Solution) 30 mg/BID | Time | Plasma Concentration (ng/mL) (QD Capsule) 60 mg QD |
| --- | --- | --- | --- |
| 13th dose | 7.76 | 7th dose | 7.83 |
| 1 | 7.51 | 2.0 | 7.42 |
| 2 | 11.28 | 4.0 | 10.11 |
| 3 | 15.22 | 6.0 | 10.03 |
| 4 | 16.28 | 8.0 | 11.98 |
| 6 | 13.77 | 10.0 | 14.85 |
| 8 | 10.75 | 12.0 | 15.30 |
| 10 | 9.03 | 15.0 | 12.77 |
| 12 (14th dose) | 7.07 | 18.0 | 10.03 |
| 13 | 6.50 | 21.0 | 8.54 |
| 14 | 8.59 | 24.0 | 7.50 |
| 15 | 11.85 | 27.0 | 7.06 |
| 16 | 13.47 | | |
| 18 | 11.84 | | |
| 20 | 10.11 | | |
| 22 | 8.32 | | |
| 24 | 7.87 | | |

The Mean values for the following pharmacokinetic parameters were determined from the plasma concentration time profiles: AUC=Area under the curve, Cmax=Maximum plasma concentration, Cmin=minimum plasma concentration, Ratio=ratio of C-max to C-min, Tmax=time to maximum concentration, and F=relative bioavailability as compared to the instant release tablet. The means values for the tablet and the sustained release clentiazem capsules described above are listed in Table XI.

TABLE XI

| Pharmacokinetic Parameter (LS Means) | Oral Solution | SR Capsule |
| --- | --- | --- |
| AUC | 260.79 ng.hr/mL | 251.31 ng.h/mL |
| Cmax | 16.97 ng/mL | 15.65 ng/mL |
| Cmin | 6.83 ng/mL | 6.66 ng/ml |
| Ratio | 2.57 | 2.53 |
| Tmax | 3.66 hours | 10.79 hours |
| F | 1.0 | 0.97 |

In Table XI, Cmin is the Mean Steady state trough level for days 6, 7 and 8 of the study. The ratio is determined within individual subjects and the F is based on matched subjects in the design.

This sustained release capsule formulation containing multi-layered SR beads was considered to be a once-a-day formulation based on the acceptable relative bioavailability, acceptable minimum concentration and acceptable ratio of maximum concentration to minimum concentration.

Conclusion

The present invention is thus provided. Numerous adaptations and modifications can be effected by those skilled in the art within the spirit of this invention, the scope of which is particularly pointed out by the following distinctly claimed subject matter.

What is claimed is:

1. A controlled releasing drug bead comprising components of:
   1) a multi-layered inner core, and
   2) a multi-layered periphery,
   said core containing at least (A) an inner portion having carboxylic acid selected from the group consisting of succinic acid, maleic acid, adipic acid, malic acid, tartaric acid and citric acid and (B) a sustainably-acid-releasing coating thereover,
   said periphery containing at least (A) an inner portion having a mixture of at least (i) a benzothiazepine compound (ii) a surface active agent (iii) a sustainably-drug-releasing coating thereover,
   said bead effective for the controlled release of the pharmaceutical compound into a physiological environment having a high pH.

2. The bead of claim 1 wherein the acid is succinic acid.

3. The bead of claim 2 wherein the surface active agent is sodium laurel sulfate.

4. The bead of claim 3 wherein the benzothiazepine compound is clentiazem.

5. The bead of claim 1 wherein said sustainably-drug-releasing coating permits rapid release of said pharmaceutical compound in an aqueous medium.

6. A process for preparing a controlled release pharmaceutical drug bead comprising building up an inner core portion having a carboxylic acid selected from the group consisting of succinic acid, maleic acid, adipic acid, malic acid, tartaric acid and citric acid, coating it with a sustainably acid-releasing coating to provide a multi-layered core, building upon said core an inner periphery of a mixture of at least a benzothiazepine compound and a surface active agent and coating it with a sustainably drug-releasing coating.

7. The process of claim 6 wherein the acid is succinic acid.

8. The process of claim 7 wherein the surface active agent is sodium laurel sulfate.

9. The process of claim 8 wherein the benzothiazepine compound is clentiazem.

10. The process of claim 1 wherein said sustainably-drug-releasing coating permits rapid release of said pharmaceutical compound in an aqueous medium.

11. A method for administering a benzothiazepine compound to a patient in need thereof comprising orally ingesting a sample of controlled release drug bead of claim 1.

* * * * *

UNITED STATES PATENT AND TRADEMARK OFFICE
CERTIFICATE OF CORRECTION

PATENT NO. : 5,320,853
DATED : June 14, 1994
INVENTOR(S) : Noda, K. et al.

It is certified that error appears in the above-identified patent and that said Letters Patent is hereby corrected as shown below:

Title Page, Item [73]

"Assignee: Merrell Dow Pharmaceuticals Inc.
    Cincinnati, Ohio"
 and should read
  -- Assignee: Tanabe-Marion Laboratories
             Japan --

Signed and Sealed this

Thirteenth Day of February, 1996

Attest:

BRUCE LEHMAN

*Attesting Officer*   *Commissioner of Patents and Trademarks*